(12) United States Patent
Weiner

(10) Patent No.: US 6,643,015 B2
(45) Date of Patent: Nov. 4, 2003

(54) SYSTEM, METHOD, AND PRODUCT FOR SYMMETRICAL FILTERING IN SCANNING OF BIOLOGICAL MATERIALS

(75) Inventor: Nathan K. Weiner, Stoughton, MA (US)

(73) Assignee: Affymetrix, Inc., Santa Clara, CA (US)

( * ) Notice: Subject to any disclaimer, the term of this patent is extended or adjusted under 35 U.S.C. 154(b) by 134 days.

(21) Appl. No.: 09/683,219

(22) Filed: Dec. 3, 2001

(65) Prior Publication Data

US 2002/0159058 A1 Oct. 31, 2002

Related U.S. Application Data

(60) Provisional application No. 60/286,578, filed on Apr. 26, 2001.

(51) Int. Cl.⁷ .............................. G01J 3/30; G01N 21/64
(52) U.S. Cl. ..................... 356/318; 436/172; 422/82.08
(58) Field of Search ........................... 356/318; 702/27; 250/458.1–461.2; 422/82.05–82.08; 436/171–172

(56) References Cited

U.S. PATENT DOCUMENTS

| | | | |
|---|---|---|---|
| 4,410,799 A | 10/1983 | Okamoto | |
| 4,758,727 A | 7/1988 | Tomei et al. | |
| 4,855,597 A | 8/1989 | Shimura | |
| 4,877,966 A | 10/1989 | Tomei et al. | |
| 5,032,720 A | 7/1991 | White | |
| 5,121,138 A | 6/1992 | Schermer et al. | |
| 5,143,854 A | 9/1992 | Pirrung et al. | |
| 5,302,824 A | 4/1994 | Prager | |
| 5,371,361 A | * 12/1994 | Arends et al. | 250/235 |
| 5,528,050 A | 6/1996 | Miller et al. | |
| 5,538,613 A | 7/1996 | Brumley et al. | |
| 5,578,832 A | 11/1996 | Trulson et al. | |
| 5,631,734 A | 5/1997 | Stern et al. | |
| 5,689,110 A | 11/1997 | Dietz et al. | |
| 5,834,758 A | 11/1998 | Trulson et al. | |
| 5,895,915 A | 4/1999 | DeWeerd et al. | |
| 5,936,324 A | 8/1999 | Montagu | |
| 5,981,956 A | 11/1999 | Stern | |
| 5,984,474 A | 11/1999 | Schweitzer et al. | |
| 6,025,601 A | 2/2000 | Trulson et al. | |
| 6,075,613 A | 6/2000 | Schermer et al. | |

(List continued on next page.)

FOREIGN PATENT DOCUMENTS

| | | |
|---|---|---|
| EP | 1 186 673 A2 | 3/2002 |
| WO | WO 98/35223 | 8/1998 |
| WO | WO 99/47964 | 9/1999 |

OTHER PUBLICATIONS

Jean Montagu and Nathan Weiner, Fluorescence Array Scanner Employing a Flying Objective; Journal of the Association for Laboratory Automation, Mar. 1999, vol. 4, No. 1.

*Primary Examiner*—F. L. Evans
*Assistant Examiner*—Kara Geisel
(74) *Attorney, Agent, or Firm*—Philip L. McGarrigle; Alan Sherr

(57) ABSTRACT

An apparatus is described that includes an emission signal detector and an emission signal filter. An excitation beam scans an array of biological materials, and the emission signal detector detects an emission signal indicative of an emission beam responsive to the excitation beam. The emission signal filter is a linear-phase filter that provides a filtered emission signal having substantially symmetrical rise and fall edges. A linear-phase excitation signal filter may also be provided that provides a filtered excitation signal having substantially symmetrical rise and fall edges. The emission signal filter and the excitation signal filter may be matched. In some applications, they may be high-order Bessel filters. Linear-phase filtering enables sampling of emission signals to be accomplished consistently irrespective of the scanning direction, and thus is particularly advantageous in bi-directional scanning applications.

32 Claims, 12 Drawing Sheets

U.S. PATENT DOCUMENTS

| | | |
|---|---|---|
| 6,078,390 A | 6/2000 | Bengtsson |
| 6,097,025 A | 8/2000 | Modlin et al. |
| 6,130,440 A | 10/2000 | Ogura |
| 6,141,096 A | 10/2000 | Stern et al. |
| 6,166,385 A | 12/2000 | Webb et al. |
| 6,169,289 B1 | 1/2001 | White et al. |
| 6,171,793 B1 | 1/2001 | Phillips et al. |
| 6,185,030 B1 | 2/2001 | Overbeck |
| 6,201,639 B1 | 3/2001 | Overbeck |
| 6,207,960 B1 * | 3/2001 | Stern ....................... 250/458.1 |
| 6,209,983 B1 | 4/2001 | Osborne et al. |
| 6,211,913 B1 | 4/2001 | Hansen et al. |
| 6,211,989 B1 | 4/2001 | Wulf et al. |
| 6,218,803 B1 | 4/2001 | Montagu et al. |
| 6,225,625 B1 | 5/2001 | Pirrung et al. |
| 6,229,607 B1 | 5/2001 | Shirai et al. |
| 6,245,507 B1 | 6/2001 | Bogdanov |
| 6,301,550 B1 * | 10/2001 | Okamoto et al. ........... 702/167 |
| 6,309,601 B1 | 10/2001 | Juncosa et al. |
| 6,312,914 B1 | 11/2001 | Kardos et al. |
| 6,353,475 B1 | 3/2002 | Jensen et al. |
| 2002/0074512 A1 * | 6/2002 | Montagu et al. ......... 422/82.08 |

* cited by examiner

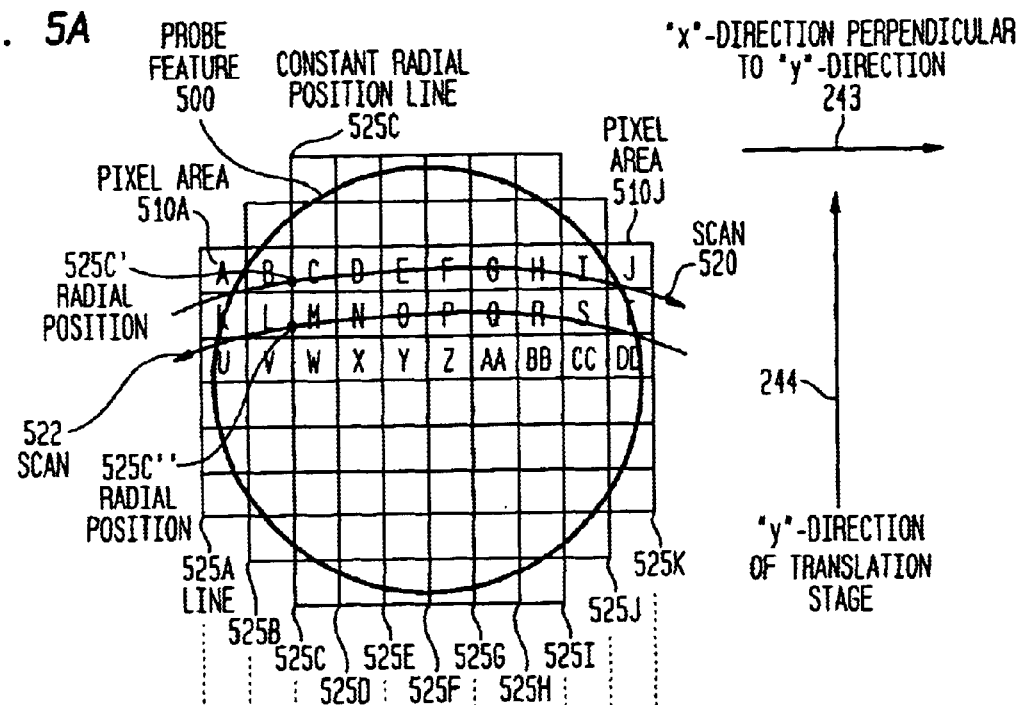
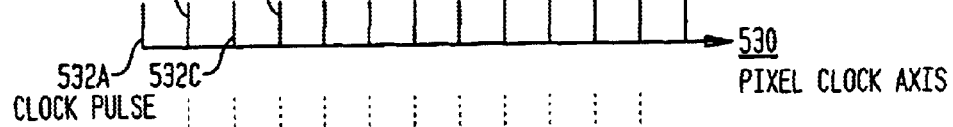
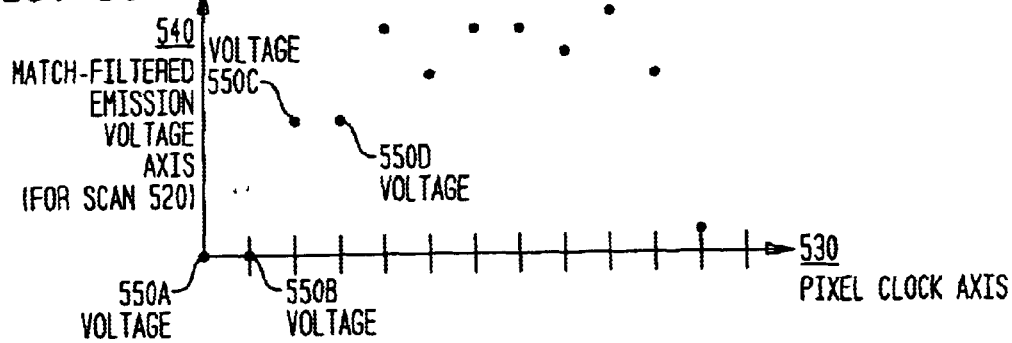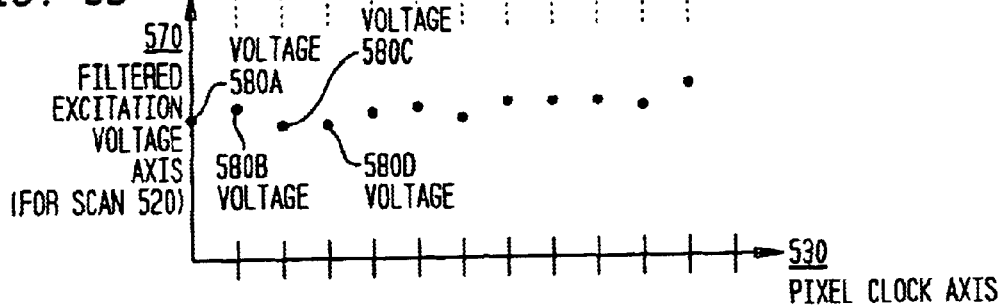

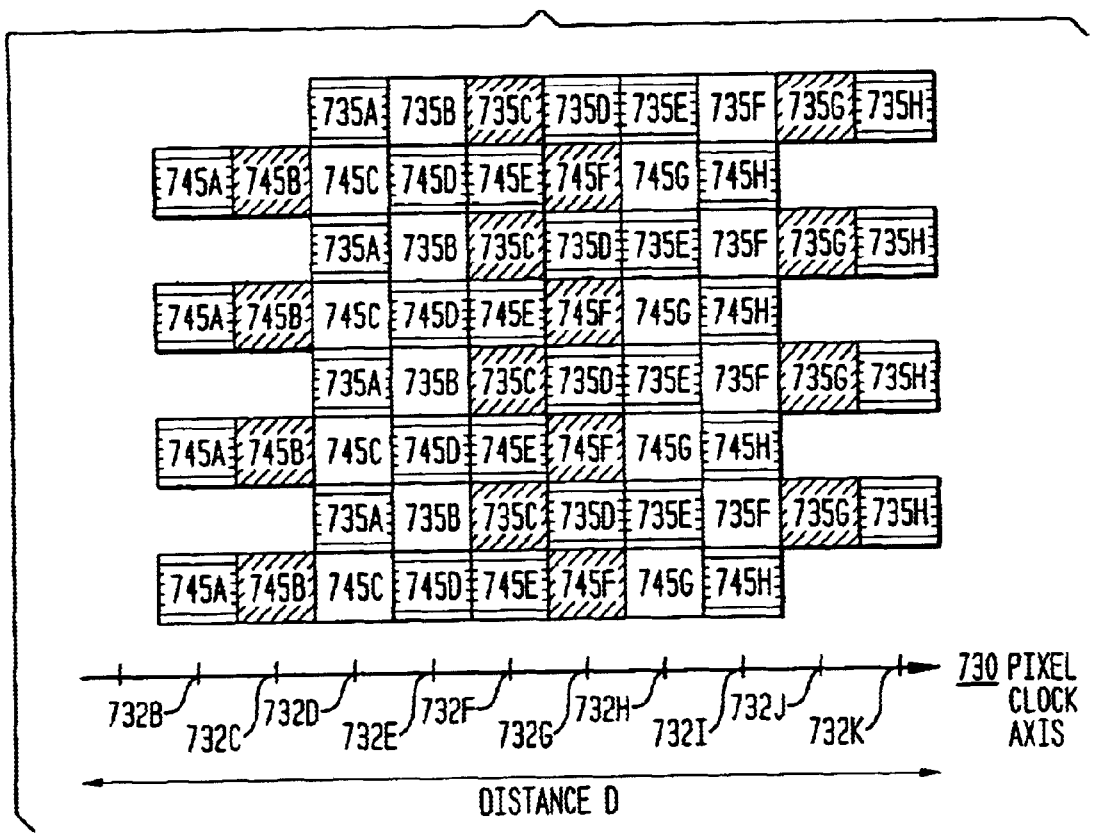

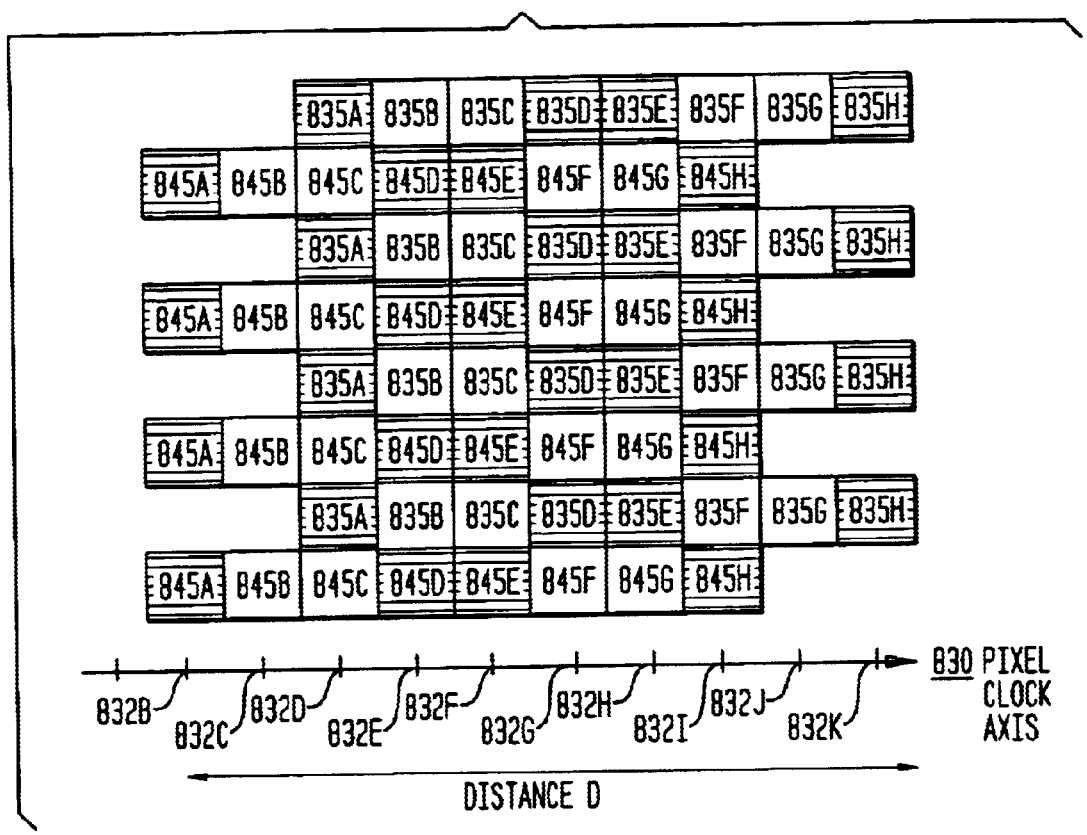

SYSTEM, METHOD, AND PRODUCT FOR SYMMETRICAL FILTERING IN SCANNING OF BIOLOGICAL MATERIALS

CROSS REFERENCE TO RELATED APPLICATIONS

The present application claims priority from U.S. Provisional Patent Application Serial No. 60/286,578, filed Apr. 26, 2001, which is hereby incorporated by reference herein in its entirety for all purposes. The present application is related to a U.S. patent application Ser. No. 09/683,216 entitled System, Method, and Product for Dynamic Noise Reduction in Scanning of Biological Materials, attorney docket number 3404.1, and to a U.S. patent application Ser. No. 09/683,217 entitled System, Method, and Product for Pixel Clocking in Scanning of Biological Materials, attorney docket number 3404.2, both of which are filed concurrently herewith and both of which are hereby incorporated by reference herein in their entireties for all purposes.

BACKGROUND OF INVENTION

1. Field of the Invention

The present invention relates to optical scanning systems for examining biological material and, in particular, to filtering emission signals from fluorescently tagged biological materials that have been excited by lasers.

2. Related Art

Synthesized nucleic acid probe arrays, such as Affymetrix® GeneChip® synthesized probe arrays, have been used to generate unprecedented amounts of information about biological systems. For example, a commercially available GeneChip® array set from Affymetrix, Inc. of Santa Clara, Calif., is capable of monitoring the expression levels of approximately 6,500 murine genes and expressed sequence tags (EST's). Experimenters can quickly design follow-on experiments with respect to genes, EST's, or other biological materials of interest by, for example, producing in their own laboratories microscope slides containing dense arrays of probes using the Affymetrix® 417™ or 427™ Arrayers or other spotting devices. Analysis of data from experiments with synthesized and/or spotted probe arrays may lead to the development of new drugs and new diagnostic tools.

In some conventional applications, this analysis begins with the capture of fluorescent signals indicating hybridization of labeled target samples with probes on synthesized or spotted probe arrays. The devices used to capture these signals often are referred to as scanners. Due to the relatively small emission signals sometimes available from the hybridized target-probe pairs, the presence of background fluorescent signals, the high density of the arrays, variations in the responsiveness of various fluorescent labels, and other factors, care must be taken in designing scanners to properly acquire and process the fluorescent signals indicating hybridization. For example, U.S. Pat. No. 6,171,793 to Phillips, et al., hereby incorporated herein in its entirety for all purposes, describes a method for scanning probe arrays to provide data having a dynamic range that exceeds that of the scanner. As another example, U.S. patent application Ser. No. 09/681,819, filed Jun. 11, 2001 and hereby incorporated herein by reference in its entirety for all purposes, describes systems and methods for aligning grids on scanned images to provide appropriate pixel analysis. Nonetheless, there is a continuing need to improve scanner design to provide more accurate and reliable fluorescent signals and thus provide experimenters with more sensitive and accurate data.

SUMMARY OF INVENTION

High-density probe arrays allow higher throughput and other advantages as compared to probe arrays of lower densities. However, as the density of probes grows, the difficulties also generally increase of accurately and reliably distinguishing adjacent probes and collecting sufficient image information, i.e., pixels, specific to each probe. Similar difficulties emerge as the goal of higher throughput results in faster image scans. There thus is a need for methods and systems for scanning high-density probe arrays, possibly at higher scanning speeds, but yet preserving high sensitivity, accuracy, and reliability with respect to the acquisition of image pixels.

Systems, methods, and products to address these and other needs are described herein with respect to illustrative, non-limiting, implementations. Various alternatives, modifications and equivalents are possible. For example, certain systems, methods, and computer software products are described herein using exemplary implementations for analyzing data from arrays of biological materials produced by the Affymetrix® 417™ or 427™ Arrayer. Other illustrative implementations are referred to in relation to data from Affymetrix ® GeneChip® probe arrays. However, these systems, methods, and products may be applied with respect to many other types of probe arrays and, more generally, with respect to numerous parallel biological assays produced in accordance with other conventional technologies and/or produced in accordance with techniques that may be developed in the future. For example, the systems, methods, and products described herein may be applied to parallel assays of nucleic acids, PCR products generated from cDNA clones, proteins, antibodies, or many other biological materials. These materials may be disposed on slides (as typically used for spotted arrays), on substrates employed for GeneChip® arrays, or on beads, optical fibers, or other substrates or media. Moreover, the probes need not be immobilized in or on a substrate, and, if immobilized, need not be disposed in regular patterns or arrays. For convenience, the term probe array will generally be used broadly hereafter to refer to all of these types of arrays and parallel biological assays.

In accordance with one preferred embodiment, an apparatus is described for scanning probe arrays. The apparatus includes an excitation filter that filters one or more excitation signals, and an emission filter that filters one or more emission signals. The excitation filter and the emission filter of this embodiment are linear-phase filters. The terms excitation signal and emission signal will be understood in this context to refer to sets of analog or digital values indicative of the power or other measure of all or portions of excitation beams and resulting emission beams, respectively. The terms excitation beam and emission beam are intended to have broad meanings, as described below. Thus, as one non-limiting example, a first emission signal may be generated by an emission detector (such as a photodiode) and represent fluorescent emissions from fluorophores excited by an excitation beam during a first scan of a portion of a probe array. As noted below, a scan may refer to relative movement of the excitation beam with respect to the probe array along a line or an arc. A second emission signal may represent emissions from the same or other fluorophores excited by the excitation beam during a second, or substantially simultaneous, scan of the same or other portion of the probe array.

In accordance with some preferred embodiments, an apparatus is described that includes an excitation beam provider, an emission signal detector, and a linear-phase emission filter. The excitation beam provider directs an excitation beam to a plurality of locations of a probe array, and the emission signal detector detects an emission signal from at least one location. The excitation beam provider may include an excitation source, such as a laser, as well as optical, mechanical, electrical, and other components (such as mirrors, scanning arms, or galvanometers, for example). The linear-phase emission filter filters the emission signal to provide a filtered emission signal having substantially symmetrical rise and fall edges. The term substantially symmetrical rise and fall edges refers to certain advantageous characteristics of the filtered waveforms, described in detail below with respect to FIGS. 7A–7E and 8A–E. These characteristics enable sampling of emission signals to be accomplished consistently irrespective of the scanning direction, and thus linear-phase emission signal filtering is particularly advantageous in bi-directional scanning applications. The word substantially is intended to connote that precise symmetry is not required and that the degree of symmetry generally depends on sampling method, sampling criteria, and other factors that will be appreciated by those of ordinary skill in the art in view of the detailed description below.

Apparatuses in accordance with these and other embodiments may also include an excitation signal detector that detects an excitation signal, and an excitation filter that provides a filtered excitation signal. The emission filter and the excitation filter may be matched with each other. Also, the emission filter may have a first delay function and the excitation filter a second delay function, and the apparatus may further include a delay compensator that compensate for any differences between the first and second delay functions.

In some implementations of these and other embodiments, the excitation filter may include a linear-phase filter that provides a filtered excitation signal having substantially symmetrical rise and fall edges. The emission filter and the excitation filter may both comprise a high-order Bessel filter, such as a sixth order, or an eleventh order, Bessel filter. The emission filter may normalize the emission signal to avoid aliasing errors, and may be, or include, a low-pass, anti-aliasing filter. One or more characteristics of the emission filter may be determined, at least in part, based on a scan rate or a resolution. A low-pass characteristic of the linear-phase emission filter may be determined, at least in part, based on applying the Nyquist criterion to a sampling rate.

The apparatus of these and other embodiments may also include a clock signal generator that digitizes the filtered emission signal, thereby providing a plurality of digitized emission values. Also included in the apparatus may be an excitation signal detector that detects an excitation signal indicative of the excitation beam, and an excitation filter that filters the excitation signal to provide a filtered excitation signal. In these implementations, the clock signal digitizes the filtered excitation signal, thereby providing a plurality of digitized excitation values. The emission filter and the excitation filter may be matched so that the plurality of digitized emission values are spatially correlated with the plurality of digitized excitation values. In some embodiments, the excitation beam is directed to the locations of the probe array so that dx/dt is substantially constant. The probe array may include a synthesized or a spotted probe array.

In accordance with other preferred embodiments, a method is described for analyzing molecules. The method includes (1) directing an excitation beam to a plurality of probe locations; (2) receiving an emission signal; (3) linear-phase filtering the emission signal to provide a filtered emission signal having substantially symmetrical rise and fall edges; and (4) analyzing molecules at one or more probe locations based, at least in part, on one or more values of the filtered emission signal. Also described in accordance with preferred embodiments is a method including detecting an emission signal from a probe array and filtering the emission signal to provide a filtered emission signal having substantially symmetrical rise and fall edges.

In yet other preferred embodiments, a noise compensation module is described having an excitation signal filter that filters at least a first and a second excitation signal and an emission signal filter that filter at least a first and a second emission signal. The excitation signal filter and the emission signal filter are linear-phase filters, the first excitation signal and corresponding first emission signal are derived from a scan in a first direction, and the second excitation signal and corresponding second emission signal are derived from a scan in a second direction that is opposite to the first direction. The excitation signal filter and the emission signal filter may be matched with each other, and both may include a high-order Bessel filter. Also described in accordance with other preferred embodiments is a method including filtering at least a first and a second excitation signal and filtering at least a first and a second emission signal. Filtering characteristics applied to the first and second excitation signals, and to the first and second emission signals, are linear-phase. The first excitation signal and corresponding first emission signal are derived from a scan in a first direction, and the second excitation signal and corresponding second emission signal are derived from a scan in a second direction that is opposite to the first direction.

Also described in accordance with various preferred embodiments is an apparatus having an emission signal detector and an emission filter. The detector detects an emission signal from at least one probe, and the emission filter filters the emission signal to provide a filtered emission signal having substantially symmetrical rise and fall edges. In further embodiments, a method is described having the steps of detecting an emission signal from at least one probe, and filtering the emission signal to provide a filtered emission signal having substantially symmetrical rise and fall edges.

The above embodiments and implementations are not necessarily inclusive or exclusive of each other and may be combined in any manner that is non-conflicting and otherwise possible, whether they be presented in association with a same, or a different, embodiment or implementation. The description of one embodiment or implementation is not intended to be limiting with respect to other embodiments and/or implementations. Also, any one or more function, step, operation, or technique described elsewhere in this specification may, in alternative implementations, be combined with any one or more function, step, operation, or technique described in the summary. Thus, the above embodiment and implementations are illustrative rather than limiting.

BRIEF DESCRIPTION OF DRAWINGS

The above and further features will be more clearly appreciated from the following detailed description when taken in conjunction with the accompanying drawings. In the drawings, like reference numerals indicate like structures or method steps and the leftmost digit of a reference numeral indicates the number of the figure in which the referenced element first appears (for example, the element 160 appears first in FIG. 1). In functional block diagrams, rectangles generally indicate functional elements and parallelograms generally indicate data. In method flow charts, rectangles generally indicate method steps and diamond shapes generally indicate decision elements. All of these conventions, however, are intended to be typical or illustrative, rather than limiting.

FIG. 5A is a graphical representation of one embodiment of a probe feature showing bi-directional scanning lines such as may be implemented using the scanning arm of FIGS. 2A and 2B.

FIG. 5B is an illustrative plot of pixel clock pulses aligned with the scanned probe feature of FIG. 5A to show illustrative radial position sampling points.

FIG. 5C is an illustrative plot of sampled emission voltages aligned with the pixel clock pulses of FIG. 5B.

FIG. 5D is an illustrative plot of sampled excitation voltages aligned with the pixel clock pulses of FIG. 5B.

FIG. 7D is a consolidated graphical representation of pixels shown in FIGS. 7B and 7C resulting from successive bidirectional scans of a probe feature under asymmetrical filtering.

FIG. 7E is a graphical representation of the pixels of FIG. 7D shifted so as to graphically compensate for the effects of phase delay.

FIG. 8D is a consolidated graphical representation of pixels shown in FIGS. 8B and 8C resulting from successive bidirectional scans of a probe feature under symmetrical filtering.

FIG. 8E is a graphical representation of the pixels of FIG. 8D shifted so as to graphically compensate for the effects of phase delay.

DETAILED DESCRIPTION

Many scanner designs may be used in connection with the filter method and system described herein. In reference to the illustrative implementation of FIG. 1, the term excitation beam refers to light beams generated by lasers. However, excitation sources other than lasers may be used in alternative implementations. Thus, the term excitation beam is used broadly herein. The term emission beam also is used broadly herein. A variety of conventional scanners detect fluorescent or other emissions from labeled target molecules or other material associated with biological probes. Other conventional scanners detect transmitted, reflected, or scattered radiation from such targets. These processes are sometimes generally and collectively referred to hereafter for convenience simply as involving the detection of emission beams. Various detection schemes are employed depending on the type of emissions and other factors. A typical scheme employs optical and other elements to provide an excitation beam, such as from a laser, and to selectively collect the emission beams. Also generally included are various light-detector systems employing photodiodes, charge-coupled devices, photomultiplier tubes, or similar devices to register the collected emission beams. For example, a scanning system for use with a fluorescently labeled target is described in U.S. Pat. Nos. 5,143,854 and 6,225,625, hereby incorporated by reference in their entireties for all purposes. Other scanners or scanning systems are described in U.S. Pat. Nos. 5,578,832; 5,631,734; 5,834,758; 5,936,324; 5,981,956; 6,025,601; 6,141,096; 6,185,030; 6,201,639; and 6,218,803 and in PCT Application PCT/US99/06097 (published as WO99/47964), each of which also is hereby incorporated by reference in its entirety for all purposes.

Scanner Optics and Detectors 100.

Figure 1:
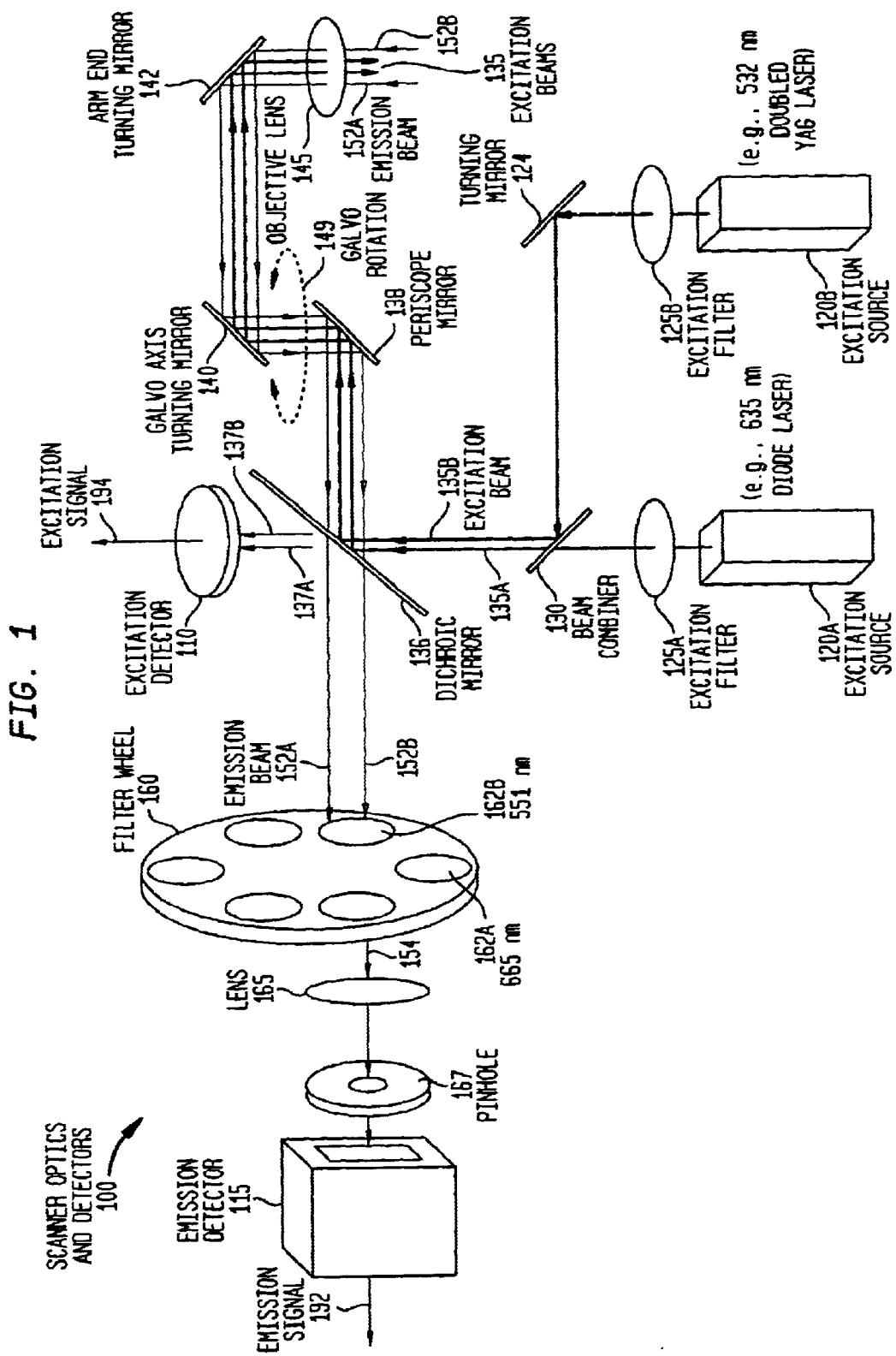
FIG. 1 is a simplified graphical representation of an illustrative arrangement of scanner optics and detectors.

FIG. 1 is a simplified graphical representation of illustrative scanner optics and detectors (hereafter, simply scanner optics) 100. Scanner optics 100 includes excitation sources 120A and 120B (generally and collectively referred to as excitation sources 120). Any number of one or more excitation sources 120 may be used in alternative embodiments. In the present example, sources 120 are lasers; in particular, source 120A is a diode laser producing red laser light having a wavelength of 635 nanometers and source 120B is a doubled YAG laser producing green laser light having a wavelength of 532 nanometers. Further references herein to sources 120 generally will assume for illustrative purposes that they are lasers, but, as noted, other types of sources, e.g., x-ray sources, may be used in other implementations.

In the illustrated implementation, it is assumed that only one of excitation sources 120A and 120B is operational (in the sense of generating an excitation beam 135) at any particular time. For example, source 120A and not source 120B may be operational for one arc scan by scanner optics 100, as described below, and source 120B and not source 120A may be operational for a subsequent scan. Sources 120A and 120B may alternate between successive scans, groups of successive scans, or between full scans of an array. For clarity, excitation beams 135A and 135B are shown as distinct from each other in FIG. 1. However, in practice, turning mirror 124 and/or other optical elements (not shown) typically are adjusted to provide that these beams follow the same path. Moreover, it also will be understood that the assumption that only one laser is operational at a time is made only for the sake of convenience and clarity of illustration. Implementations are contemplated that include simultaneous operation of any number of excitation sources 120. Beams 135 in simultaneous operation typically, but need not, follow the same path. Handbook of Biological Confocal Microscopy (James B. Pawley, ed.) (2.ed.; 1995; Plenum Press, N.Y.), which includes information known to those of ordinary skill in the art regarding the use of lasers and associated optics, is hereby incorporated herein by reference in its entirety.

Scanner optics 100 also includes excitation filters 125A and 125B that optically filter beams from excitation sources 120A and 120B, respectively. Filters 125 optionally are used to remove light at wavelengths other than the desired wavelengths, and need not be included if, for example, sources 120A and 120B do not produce light at these extraneous wavelengths. As noted, however, it may be desirable in some applications to use inexpensive lasers and often it is cheaper to filter out-of-mode laser emissions than to design the laser to avoid producing such extraneous emissions.

The filtered excitation beams from sources 120A and 120B are combined in accordance with any of a variety of known techniques. For example, one or more mirrors, such as turning mirror 124, may be used to direct filtered beam from source 120A through beam combiner 130. The filtered beam from source 120B is directed at an angle incident upon beam combiner 130 such that the beams combine in accordance with optical properties techniques well known to those of ordinary skill in the relevant art. Most of combined excitation beams 135A and 135B (generally and collectively referred to as beams 135) are reflected by dichroic mirror 136 and thence directed to periscope mirror 138 of the illustrative example. However, dichroic mirror 136 has characteristics selected so that portions of beams 135A and 135B, referred to respectively as partial excitation beams 137A and 137B and generally and collectively as beams 137, pass through it so that they may be detected by excitation detector 110.

Detector 110 may be any of a variety of conventional devices for detecting partial excitation beams 137, such as a silicon detector for providing an electrical signal representative of detected light, a photodiode, a charge-coupled device, a photomultiplier tube, or any other detection device for providing a signal indicative of detected light that is now available or that may be developed in the future. Detector 110 generates excitation signal 194 that represents detected partial excitation beams 137A or 137B. In accordance with known techniques, the amplitude, phase, or other characteristic of excitation signal 194 is designed to vary in a known or determinable fashion depending on the power of excitation beam 135. The term power in this context refers to the capability of beam 135 to evoke emissions. For example, the power of beam 135 typically may be measured in milliwatts of laser energy with respect to the illustrated example in which the laser energy evokes a fluorescent signal. Thus, excitation signal 194 has values that represent the power of beam 135 during particular times or time periods.

In the illustrated example, excitation beams 135 are directed via periscope mirror 138 and arm end turning mirror 142 to an objective lens 145. As described in greater detail below in relation to FIGS. 2A and 2B, lens 145 in the illustrated implementation is a small, light-weight lens located on the end of an arm that is driven by a galvanometer around an axis perpendicular to the plane represented by galvo rotation 149 shown in FIG. 1. Objective lens 145 thus moves in arcs over a substrate upon which biological materials have been synthesized or have been deposited. Flourophores associated with these biological materials emit emission beam 152 (beam 152A in response to excitation beam 135A, and beam 152B in response to excitation beam 135B) at characteristic wavelengths in accordance with well known principles. Emission beam 152 in the illustrated example follows the reverse path as described with respect to excitation beam 135 until reaching dichroic mirror 136. In accordance with well known techniques and principles, the characteristics of mirror 136 are selected so that beam 152 (or a portion of it) passes through the mirror rather than being reflected.

In the illustrated implementation, filter wheel 160 is provided to filter out spectral components of emission beam 152 that are outside of the emission band of the fluorophore. The emission band is determined by the characteristic emission frequencies of those fluorophores that are responsive to the frequency of excitation beam 135. Thus, for example, excitation beam 135A from source 120A, which is illustratively assumed to have a wavelength of 635 nanometers, excites certain fluorophores to a much greater degree than others. The characteristic emission wavelength of a first illustrative fluorophore (not shown in FIG. 1) when excited by beam 135A is assumed to be 665 nanometers. Emission beam 152A in this example typically will also include wavelengths above and below 665 nanometers in accordance with distributions that are known to those of ordinary skill in the relevant art. Similarly, the characteristic emission wavelength of a second illustrative fluorophore (not shown in FIG. 1), when excited by beam 135A having a wavelength of 532 nanometers, is illustratively assumed to be 551 nanometers. Thus, when excitation source 120A is operational, filter wheel 160 is turned so that filter 162A is selected (typically under computer control) and wavelengths other than 665 nanometers are removed from filtered emission beam 154. Similarly, filter 162B is selected when source 120B is operational so that wavelengths other than 551 nanometers are filtered out of beam 152B to produce filtered emission beam 154. In accordance with techniques well known to those of ordinary skill in the relevant arts, including that of confocal microscopy, beam 154 may be focused by various optical elements such as lens 165 and also passed through illustrative pinhole 167 or other element to limit the depth of field, and thence impinges upon emission detector 115.

Similar to excitation detector 110, emission detector 115 may be a silicon detector for providing an electrical signal representative of detected light, or it may be a photodiode, a charge-coupled device, a photomultiplier tube, or any other detection device that is now available or that may be developed in the future for providing a signal indicative of detected light. Detector 115 generates emission signal 192 that represents filtered emission beam 154 in the manner noted above with respect to the generation of excitation signal 194 by detector 110. Emission signal 192 and excitation signal 194 are provided to noise compensation module 310 for processing, as described below in relation to FIGS. 3 and 4.

Figure 2A:
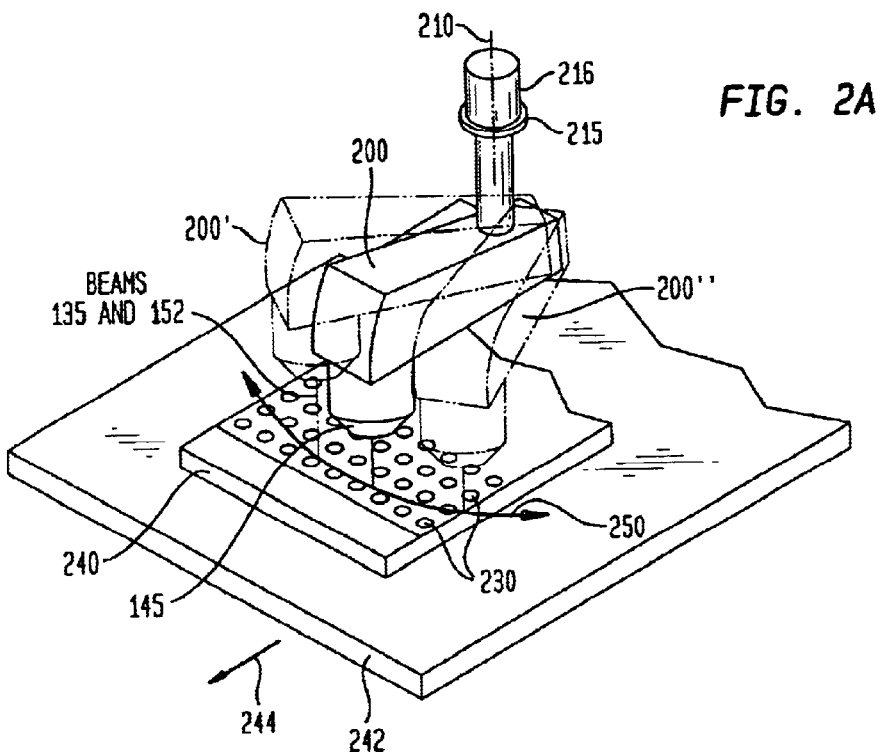
FIG. 2A is a perspective view of a simplified exemplary configuration of a scanning arm portion of the scanner optics and detectors of FIG. 1.

FIG. 2A is a perspective view of a simplified representation of an illustrative scanning arm portion of scanner optics 100 in accordance with this particular, non-limiting, implementation. Arm 200 moves in arcs around axis 210, which is perpendicular to the plane of galvo rotation 149. A position transducer 215 is associated with galvanometer 215 that, in the illustrated implementation, moves arm 200 in bi-directional arcs. Transducer 215, in accordance with any of a variety of known techniques, provides an electrical signal indicative of the radial position of arm 200. Certain non-limiting implementations of position transducers for galvanometer-driven scanners are described in U.S. Pat. No. 6,218,803 to Montagu, et al., which is hereby incorporated by reference in its entirety for all purposes. As described below, the signal from transducer 215 is provided in the illustrated implementation to computer 350 so that clock pulses may be provided for digital sampling of emission signals when arm 200 is in certain positions along its scanning arc.

Figure 2B:
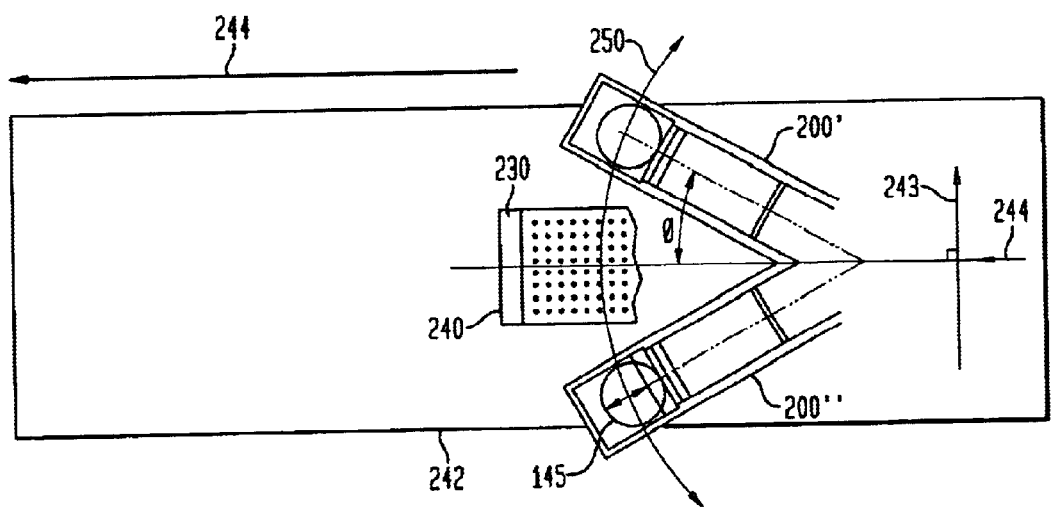
FIG. 2B is a top planar view of the scanning arm of FIG. 2A as it scans biological features on one embodiment of a probe array being moved by a translation stage under the arm's arcuate path.

Arm 200 is shown in alternative positions 200' and 200" as it moves back and forth in scanning arcs about axis 210. Excitation beams 135 pass through objective lens 145 on the end of arm 200 and excite fluorophores that may be contained in hybridized probe-target pairs in features 230 on a substrate of probe array 240, as further described below. The arcuate path of excitation beams 135 over probe array 240 is schematically shown for illustrative purposes as path 250. Emission beams 152 pass up through objective lens 145 as noted above. Probe array 240 of this example is disposed on translation stage 242 that is moved in direction 244 so that arcuate path 250 repeatedly crosses the plane of probe array 240. As is evident, the resulting coverage of excitation beams 135 over the plane of probe array 240 is therefore determined by the footprint of beam, the speed of movement in direction 244, and the speed of the scan. FIG. 2B is a top planar view of arm 200 with objective lens 145 scanning features 230 on probe array 240 as translation stage 242 is moved under path 250. As shown in FIG. 2B, arcuate path 250 of this example is such that arm 200 has a radial displacement of θ in each direction from an axis parallel to direction 244. For convenience of reference below, a direction 243 perpendicular to direction 244 is also shown in FIG. 2B. For illustrative purposes, direction 243 may hereafter be referred to as the x direction, and direction 244 as the y direction.

Further details of confocal, galvanometer-driven, arcuate, laser scanning instruments suitable for detecting fluorescent emissions are provided in PCT Application PCT/US99/06097 (published as WO99/47964) and in U.S. Pat. Nos. 6,185,030; 6,201,639; and 6,225,625, all of which have been incorporated by reference above.

Probe Array 240.

Probe array 240 as shown in FIGS. 2A and 2B is illustrative only and it will be understood that numerous variations are possible with respect to providing biological materials for scanning. For example, Affymetrix® GeneChip® arrays commercially available from Affymetrix, Inc., of Santa Clara, Calif., referred to above, are synthesized in accordance with techniques sometimes referred to as VLSIPS™ (Very Large Scale Immobilized Polymer Synthesis) technologies. Probe arrays developed with these technologies, and others that are now available and may in the future be developed for synthesizing arrays of biological materials, may hereafter be referred to for convenience as synthesized probe arrays. This term refers generally to arrays in which probes have been built in situ on an array substrate, as contrasted, for to arrays in which pre-synthesized or pre-selected probes are deposited or positioned on or within a substrate.

Some aspects of VLSIPS™ technologies are described in the following U.S. Pat. No. : 5,143,854 to Pirrung, et al.; U.S. Pat. No. 5,445,934 to Fodor, et al.; U.S. Pat. No. 5,744,305 to Fodor, et al.; U.S. Pat. No. 5,831,070 to Pease, et al.; U.S. Pat. No. 5,837,832 to Chee, et al.; U.S. Pat. No. 6,022,963 to McGall, et al.; and U.S. Pat. No. 6,083,697 to Beecher, et al. Each of these patents is hereby incorporated by reference in its entirety. The probes of these arrays typically consist of oligonucleotides that typically are synthesized by methods that include the steps of activating regions of a substrate and then contacting the substrate with a selected monomer solution. The regions are activated with a light source shown through a mask in a manner similar to photolithographic techniques used in the fabrication of integrated circuits. Other regions of the substrate remain inactive because the mask blocks them from illumination. By repeatedly activating different sets of regions and contacting different monomer solutions with the substrate, a diverse array of polymers is produced on the substrate. A variety of other techniques also exist for synthesizing probe arrays. For example, U.S. Pat. Nos. 5,885,837 and 6,040,193 describe the use of micro-channels or micro-grooves on a substrate, or on a block placed on a substrate, to synthesize arrays of biological materials.

As noted, techniques also exist for depositing or positioning pre-synthesized or pre-selected probes on or within a substrate or support. For convenience, probe arrays made in accordance with these other techniques, or depositing/positioning techniques that may be developed in the future, may hereafter be referred to as spotted arrays. Typically, spotted arrays are commercially fabricated on microscope slides. These arrays typically consist of liquid spots containing biological material of potentially varying compositions and concentrations. For instance, a spot in the array may include a few strands of short polymers, such as oligonucleotides in a water solution, or it may include a high concentration of long strands of polymers, such as complex proteins. The Affymetrix® 417™ and 427™ Arrayers are devices that deposit densely packed probe arrays of biological material on a microscope slide in accordance with these techniques. Aspects of these, and other, spot arrayers are described in U.S. Pat. Nos. 6,121,048 and 6,136,269, in PCT Applications Nos. PCT/US99/00730 (International Publication Number WO99/36760) and PCT/US 01/04285, in U.S. patent applications Ser. Nos. 09/122,216, 09/501,099, and 09/862,177, and in U.S. Provisional Patent Application Serial No. 60/288,403, all of which are hereby incorporated by reference in their entireties for all purposes. Other techniques for generating spotted arrays also exist. For example, U.S. Pat. No. 6,040,193 to Winkler, et al., is directed to processes for dispensing drops to generate spotted arrays. The '193 patent, and U.S. Pat. No. 5,885,837 to Winkler, also describe separating reactive regions of a substrate from each other by inert regions and spotting on the reactive regions. The '193 and '837 patents are hereby incorporated by reference in their entireties. Other techniques are based on ejecting jets of biological material to form spotted arrays. Other implementations of the jetting technique may use devices such as syringes or piezo electric pumps to propel the biological material.

Synthesized or spotted probe arrays typically are used in conjunction with tagged biological samples such as cells, proteins, genes or EST's, other DNA sequences, or other biological elements. These samples, referred to herein as targets, are processed so that they are spatially associated with certain probes in the probe array. For example, one or more chemically tagged biological samples, i.e., the targets, are distributed over the probe array. Some targets hybridize with at least partially complementary probes and remain at the probe locations, while non-hybridized targets are washed away. These hybridized targets, with their tags or labels, are thus spatially associated with the targets' complementary probes. The hybridized probe and target may sometimes be referred to as a probe-target pair. Detection of these pairs by scanners can serve a variety of purposes, such as to determine whether a target nucleic acid has a nucleotide sequence identical to or different from a specific reference sequence. See, for example, U.S. Pat. No. 5,837,832, referred to and incorporated above. Other uses include gene expression monitoring and evaluation (see, e.g., U.S. Pat. No. 5,800,992 to Fodor, et al.; U.S. Pat. No. 6,040,138 to Lockhart, et al.; and International App. No. PCT/US98/15151, published as WO99/05323, to Balaban, et al.), genotyping (U.S. Pat. No. 5,856,092 to Dale, et al.), or other detection of nucleic acids. The '992, '138, and '092 patents, and publication WO99/05323, are incorporated by reference herein in their entirety for all purposes for the uses stated above and all the uses that are disclosed therein.

To ensure proper interpretation of the term probe as used herein, it is noted that contradictory conventions exist in the relevant literature. The word probe is used elsewhere in some contexts to refer not to the biological material that is synthesized on a substrate or deposited on a slide, as described above, but to what has been referred to herein as the target. To avoid confusion, the term probe is used herein to refer to probes such as those synthesized according to the VLSIPS™ technology; the biological materials deposited or positioned so as to create spotted arrays; and materials synthesized, deposited, or positioned to form arrays according to other current or future technologies. Moreover, as noted, the term probe is not limited to probes immobilized in array format. Rather, the functions and methods described herein may also be employed with respect to other parallel assay devices and techniques. Also, in some cases the sequence and/or composition of the probes may not be known, or may not be fully known.

Noise Compensation Module 310.

Figure 3:
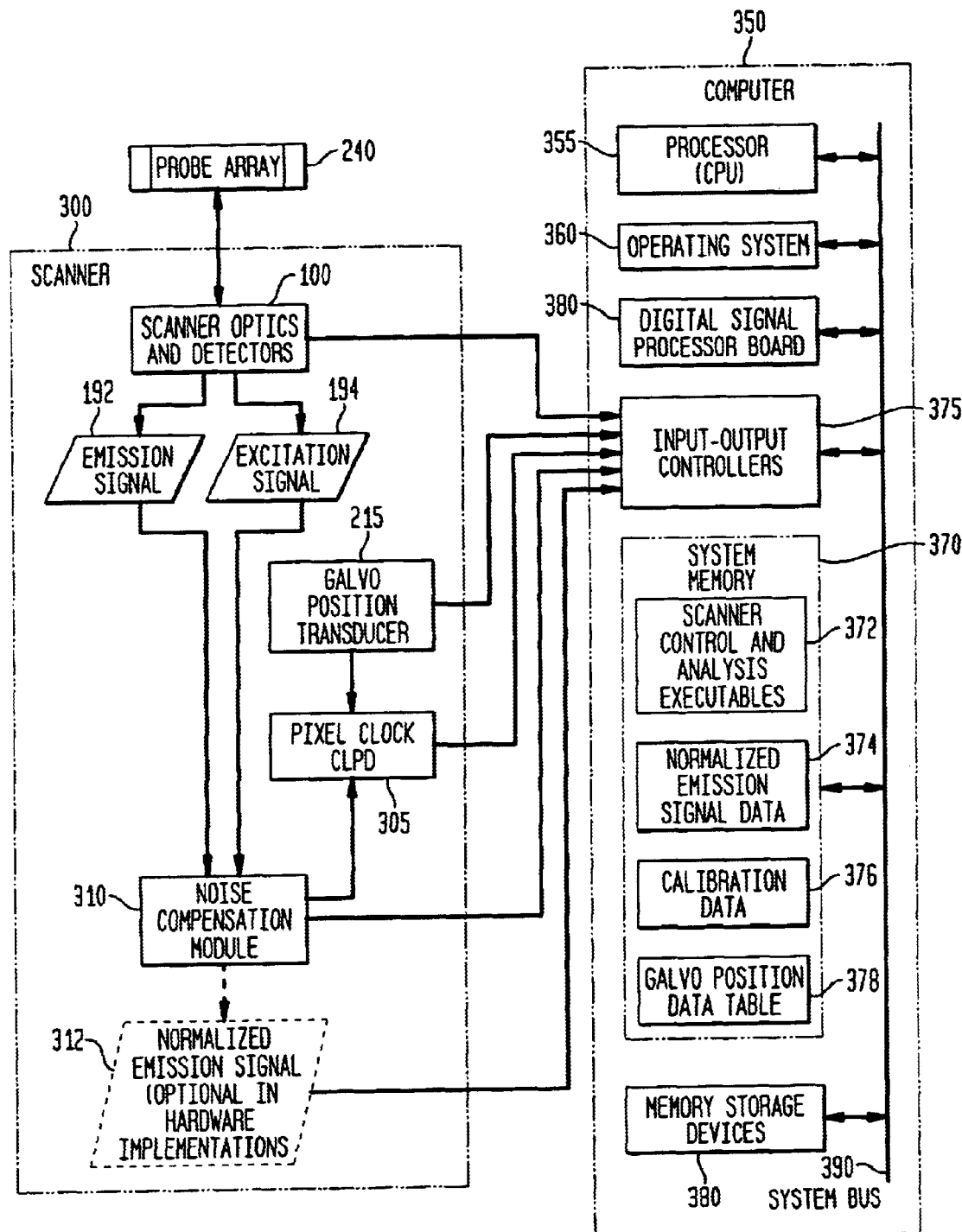
FIG. 3 is a functional block diagram of one embodiment of a scanner-computer system.
Figure 4:
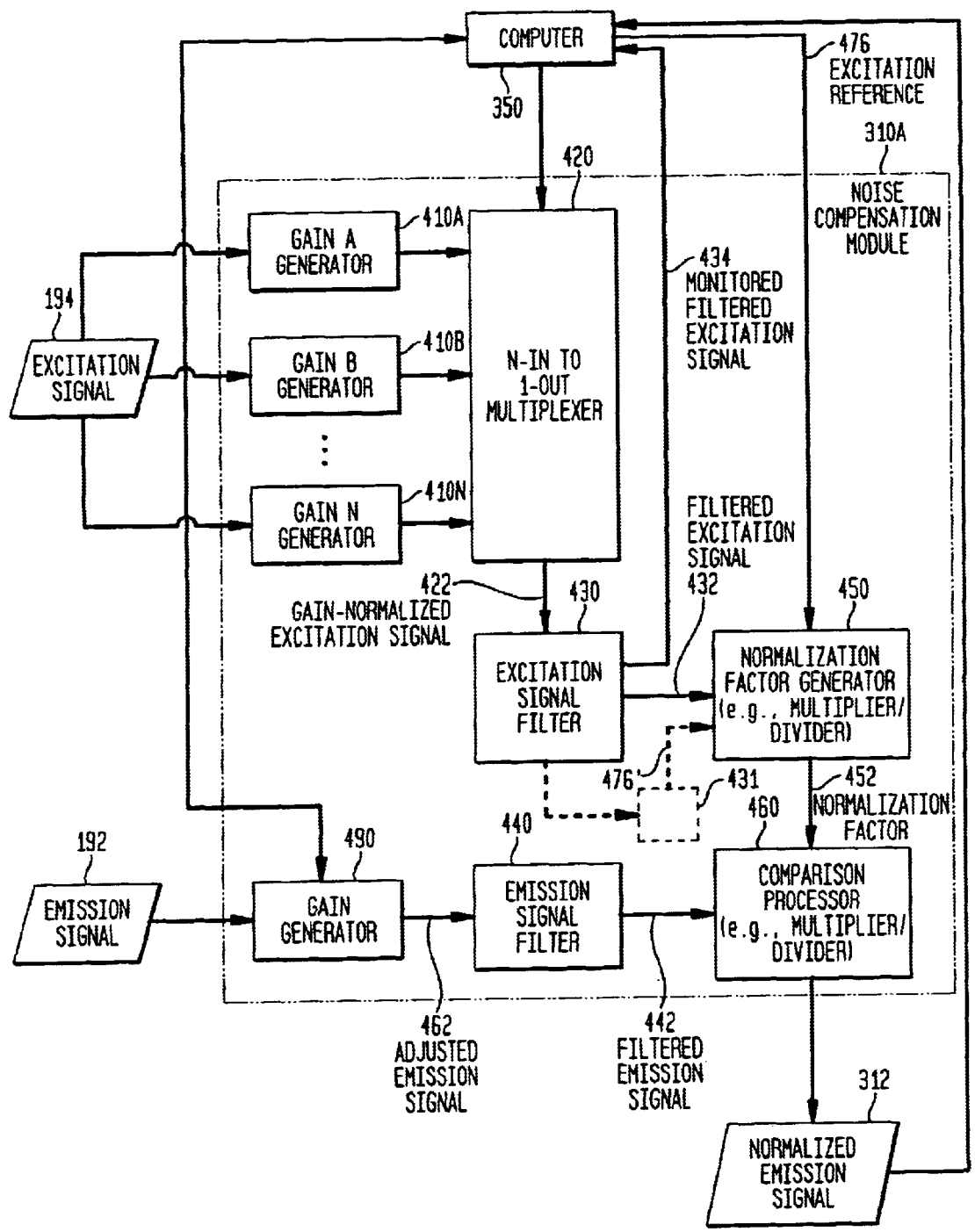
FIG. 4 is a functional block diagram of one embodiment of a noise compensation module for providing an emission signal normalized to compensate for noise in the excitation source.

FIG. 3 is a functional block diagram of a scanner-computer system showing scanner 300 under the control of computer 350. A component of scanner 300 is noise compensation module 310 that, among other things, conditions emission signals 192 and excitation signals 194 to provide bi-directional edge and feature clarification. In the illustrated implementations, this function is accomplished using an excitation signal filter having appropriate smoothing characteristics and symmetrical rise and fall characteristics, and a matched emission signal filter. In some implementations, such as shown in FIG. 4, module 310 also includes a hardware-implemented normalization factor generator 450. Generator 450 generates a normalization factor 452 that is provided to compensation processor 460. Based on normalization factor 452, processor 460 adjusts emission signals 192 for noise in excitation signals 194. The resulting normalized emission signal 312 is shown in FIG. 3 in dotted lines to emphasize that it is the product of an optional configuration. In some other embodiments, a software application executed on computer 350, together with a digital signal processor board in the computer, implement the functions of generating a compensating factor and adjusting emission signals 192 to compensate for noise in excitation signals 194. The result is normalized emission signal data 374 stored in system memory 370 of computer 350 for further processing and/or display. The functions of certain components of scanner 300 and computer 350 are interchangeable in some implementations. As a non-limiting example, some or all of the functions of digital signal processor board 380, as well as those of scanner control and analysis applications executables 372 may, in some implementations, be carried out by noise compensation module 310. The functions of module 310 are now further described, first in an example in which module 310 carries out both bi-directional edge clarification and noise compensation, and then in an example in which the latter function is carried out by software executing on computer 350.

FIG. 4 is a functional block diagram of one implementation of noise compensation module 310, referred to as module 310A. Using primarily hardware components, illustrative module 310A adjusts emission signal 192 to compensate for noise in excitation source 120, thereby providing normalized emission signal 312. Module 310A includes a series of a number N gain generators 410. Under the control of computer 350, gain generators 410 provide adjustable gains so that excitation signal 194 is normalized irrespective of excitation source. This normalization is provided to compensate for differences in the amplitude of excitation signal 194 due to differences in optical parameters of scanner optics and detectors 100 at different wavelengths of excitation beam 135. These optical parameters include the percentage of light of different wavelengths that passes through dichroic mirror 136, optical losses due to mirror reflection that may vary according to wavelength, the response characteristics of excitation detector 110 as a function of wavelength, and other factors that will be appreciated by those of ordinary skill in the relevant art.

Gain generators 410 may be implemented in accordance with any of a variety of conventional techniques, or ones that may be developed in the future, for changing the amplitude of a signal. The gains provided by each of generators 410 may be predetermined based on calibration protocols; for example, variable resistors may be adjusted by a technician during manufacture so that a standard amount of power provided by each of excitation sources 120 results in a same voltage for gain-normalized excitation signal 422. Alternatively, this adjustment function could be performed automatically by scanner control and analysis executables 372. For example, under the control of executables 372, each of excitation sources 120 may successively be enabled and a representative value of excitation signal 194 be calculated for each. In accordance with known techniques, these calculated values may be provided to generators 410 to change gain parameters to achieve signal normalization.

Module 310A also includes multiplexer 420 that, under the control of computer 350 in this implementation, selects the normalized excitation signal provided by the gain generator corresponding to the one of excitation sources 120 that is operational. For example, during a period when computer 350 has made excitation source 120A operational, and assuming for illustrative purposes that gain generator 410A has been calibrated to source 120A, then computer 350 provides an appropriate enabling or control signal to multiplexer 420 so that the signal from generator 410A is selected. Multiplexer 420 may select from any number of N inputs to provide, in the illustrated implementation, one selected output, shown in FIG. 4 as gain-normalized excitation signal 422. Any of numerous conventional or future multiplexers or switches may be used to provide this function.

Another component of module 310A in the illustrated implementation is gain generator 490. Generator 490 adjusts the gain of emission signal 192 in accordance with known techniques to provide that the input to filter 440 is within a nominal range of amplitudes or, alternatively, has a nominal steady-state component. Thus, for example, if the emissions of a particular fluorophore in a particular assay occur over a relatively small dynamic range, the emission signal from that fluorophore may optionally be adjusted by gain generator 490 to provide a proportionately larger-range signal for filtering and subsequent sampling. The magnitude of the gain adjustment may, in some implementations, be user selected. For example, a user may employ a graphical user interface (not shown) or other input technique to specify to scanner control and analysis executables 372 what the gain provided by gain generator 490 should be. This determination typically is made based on the fluorophores used in a particular assay and a list of illustrative gains that may be presented to the user in a pull down menu of the graphical user interface or in accordance with any of a variety of other known techniques. In other implementations, the gain value may be determined automatically by scanner control and analysis executables 372. For example, executables 372 may measure emission signal 192 to determine its low-frequency components, peak-to-peak amplitudes, or other indicators of dynamic range. In accordance with known techniques, executables 372 may then consult a look-up table included, for example, in calibration data 376, to compare the measured indicators with nominal values, and adjusts the gain accordingly.

Also included in noise compensation module 310A is emission filter 440. Emission filter 440 performs an anti-aliasing function so that normalized emission signal 312 may be digitized without aliasing errors. In the illustrated implementation, filter 440 is a low-pass filter. As noted, it is not uncommon for high-frequency noise to be present in the outputs of less expensive lasers, and the magnitude of this noise may constitute a substantial portion (e.g., 60%) of the magnitude of the signal. Generally, emissions of fluorophores are linearly related to their excitation throughout a range of interest in typical scanner applications. Therefore, high frequency noise from the lasers in excitation beam 135 produces high frequency noise of the same character in emission signal 192 and adjusted emission signal 462 and, of course, in excitation signal 194.

The low-pass, anti-aliasing characteristics of filter 440 are designed, in accordance with known techniques, based on a rate at which normalized emission signal 312 will be digitally sampled. This sampling rate, in turn, is based on a desired scan rate and a desired resolution of the scanned image. These considerations are now described in relation to FIGS. 5A and 5B.

FIG. 5A is a simplified graphical representation of a probe feature for detection and processing by scanner 300. Generally, the term probe feature is used in this context to refer to a region of a probe array made up one or more probes that are designed to detect a same target or portion of a target, or to provide a control to verify the detection of that target or portion of a target. In a spotted probe array, a probe feature may be a single spot of a biological material intended to contain one species of polymer. In a synthesized probe array, a probe feature may include many thousands of oligonucleotides designed for a perfect match with a same target sequence, or a probe feature may include thousands of nucleotides designed for a mismatch (for control purposes) with a same target sequence.

FIG. 5A shows idealized probe feature 500 in the form of a single circular spot that may be deposited, for example, by an Affymetrix® 417™ or 427™ Arrayer. It will be understood that a probe feature may be any shape, including irregular shapes. Spot 500 may be, as an illustrative example, one of features 230 of the spotted probe array of FIGS. 2A and 2B. In the manner described above, objective lens 145 scans over probe feature 500 (and, typically, other probe features of the probe array) in bi-directional arcs. An illustrative scan 520 is shown in FIG. 5A. It will be understood that FIG. 5A is not necessarily drawn to scale, and that the ratio of the radius of the arc of scan 520 to the radius of feature 500 is illustrative only.

Also, probe feature 500 moves under objective lens 145, as represented by direction 244 of FIGS. 2B and 5A that, as noted, may be referred to for convenience as the y direction. Thus, in the illustrated implementation, arm 200 scans in an arc in one direction, shown as left-to-right scan 520 in FIG. 5A. Translation stage 242 is then moved incrementally by a stepping motor (not shown) in y-direction 244 and arm 200 then scans back in the opposite direction, shown as right-to-left arcuate scan 522. Translation stage 242 is again moved in direction 244, and so on in scan-step-scan-step sequences. In this example, the terms scan or scan line thus will be understood to apply to a scan of a line or an arc, typically each scan referring to the movement along the line or arc in one direction. However, a scan may also be repeated in one direction, or bi-directionally, multiple times, and the terms scan or scan line may refer to these repeated scans in some contexts. Returning to the present specific example in which scans 520 and 522 are referred to as separate scans, the distance between these scans thus corresponds to the distance that translation stage 242 is moved in each increment, although it will be understood that the distance shown in FIG. 5A is not necessarily to scale and is illustrative only. It will be understood that any other combination of scanning and stepping is possible in alternative implementations, and that scanning and moving of translation stage 242 may occur at the same or at overlapping times in some implementations. Translation stage 242 need not be stepped in some implementations, but may, for example, be moved continuously.

FIG. 5B is a plot having a pixel clock axis 530 showing when clock pulses 532 occur. Axis 530 in the illustrated implementation is a spatial axis; that is, each of clock pulses 532 occurs in reference to the radial location of arm 200 during each scan, as described in greater detail below. Thus, with reference to the position of translation stage 242 indicated by scan 520, a clock pulse 532A occurs prior to arm 200 passing over feature 500 from the left as shown in FIGS. 5A and 5B. (For sake of clarity of illustration only, vertical dotted lines are provided between FIGS. 5A and 5B to illustrate this alignment.) As another example, clock pulse 532C occurs with respect to scan 520 when arm 200 has just passed over portions of feature 500 indicated by pixel areas A and K. These areas are referred to as pixel areas because a digital value is assigned to each such area in the illustrated implementation based on the strength of a filtered emission signal associated with that area. In accordance with known techniques, clock pulses 532 enable the digital sampling of the filtered emission signal.

As will be appreciated by those of ordinary skill in the relevant art, the Nyquist criterion may be applied to determine the appropriate low-pass characteristics of filter 430 based on a desired sampling rate. As noted, clock pulses 532 are spatially rather than temporally determined in the illustrated implementation. Moreover, in some aspects of the illustrated implementation, galvanometer 216 is driven by a control signal provided by computer 350 such that the velocity of arm 200 in x-direction 243 is constant in time during those times when arm 200 is over probe feature 500 (and, typically, over other features of the probe array being scanned). That is, dx/dt is a constant (and thus the angular velocity varies) over the probe-scanning portions of each arc and, in particular, it is a constant during the times when clock pulses are generated to enable digital sampling. As is evident, dx/dt must be reduced to zero between each successive scan, but this deceleration and reversal of direction takes place after arm 200 has passed over the probe feature (or, more generally, the probe array). The design and implementation of a galvanometer control signal to provide constant dx/dt are readily accomplished by those of ordinary skill in the relevant art.

Thus, the approximate sampling rate may readily be calculated based on the desired scanning speed (dx/dt) and desired pixel resolution. To provide an illustrative example, a spot deposited by an Affymetrix® 417™ Arrayer typically has a diameter of approximately 200 microns. Spotted probe arrays made using this instrument typically may be deposited over a surface having a width of about 22 millimeters on a microscope slide that is 25 millimeters wide. In order to achieve pixel resolution of about 10 microns, a sampling rate of about 160 kHz is sufficient for scanning speeds typical for scanners used with respect to these probe arrays, such as the Affymetrix® 428™ scanner. Other sampling rates, readily determined by those of ordinary skill, may be used in other applications in which, for example, different scanning speeds are used and/or different pixel resolutions are desired. The desired pixel resolution typically is a function of the size of the probe features, the possibility of variation in detected fluorescence within a probe feature, and other factors. The desired scanning speed typically is a function of the size of the probe array to be scanned, the amount of a time that a user may wish to wait for the scanning to be completed, the response characteristics of the fluorophores, the response characteristics of emission detector 115, the response and operational characteristics of galvanometer 216, and a variety of other factors.

In order to avoid aliasing errors, filter 440 should have a low-pass cutoff frequency of one half or less of the sampling frequency, as those of ordinary skill will appreciate based on the Nyquist criterion. Thus, for example, filter 440 as implemented in the Affymetrix® 428™ scanner is designed in accordance with known techniques to have a cut-off frequency of 33 kHz in some implementations and 67 kHz in other implementations. As will be evident to those of ordinary skill in the relevant art, the lower cut-off frequency achieves somewhat greater smoothing at the expense of a potential loss in signal accuracy. In implementations in which the command signal driving galvanometer 216 is not designed to provide constant dx/dt but rather, for example, a constant angular velocity over the probe-scanning area, the appropriate cut-off frequency dictated by the Nyquist criterion should take into account variation in the sampling rate for different portions of the arc assuming that it is desired to provide clock pulses that are constant in the x direction.

Noise compensation module 310A also includes excitation signal filter 430 that has the same design characteristics as, i.e., it is matched with, emission signal filter 440. The reason for matching filters 430 and 440 with each other is to provide that the delay through both filters is the same. If the delays were different, then filtered excitation signal 432 and filtered emission signal 442 would no longer be spatially correlated. That is, a value of filtered excitation signal 432 at a particular time t would represent the excitation of a particular fluorophore at a position p, but the value of filtered emission signal 442 at the same time t would represent the emission of a fluorophore that was excited at a position either before or after position p in the scanning arc.

Loss of spatial correlation could interfere with techniques described herein to normalize emission signals to compensate for noise in laser excitation signals. As described below, normalized emission signal 312 is determined in this implementation by adjusting filtered emission signal 442 by a normalization factor 452. Factor 452 is determined by comparing a nominal excitation value with filtered excitation signal 432. The nominal excitation value can be derived in a variety of such as by low-pass filtering or by taking an average or other statistical measure of large numbers of samples over a relatively long period so that the impact of noise components is minimized. Also, a nominal value can be predetermined by manual calibration or other techniques, and the value stored in calibration data 376 for reference. In essence, emission signals are adjusted to compensate for variations in the excitation signals that gave rise to them. If spatial correlation is not maintained, then this cause and effect relationship may be lost and erroneous adjustments may result. However, approaches other than matched filters may be taken to provide spatial correlation. For example, in alternative embodiments, any mismatches in the delays of filters 430 and 440 may be compensated for either in hardware (e.g., by introducing a compensating delay with respect to one or the other signal in accordance with known techniques) or in software (e.g., by realigning sampled emission and excitation signals to offset delays).

FIGS. 5A–5D further illustrate these points. In these figures, it is illustratively assumed that executables 372 initiates clock pulse 532D at a time t. This clock event is determined by the receipt of a signal from transducer 215 indicating that excitation beam 135 is located over a radial position in the scanning arc shown with reference to scan 520 as radial position 525C'. (Transducer 215 provides a signal with the same value when beam 135 is located over the same radial position for scan 522, which is labeled as radial position 525C".) Executables 372 retrieves from galvo position data table 378 a value of the signal from transducer 215 that corresponds to radial positions 525C' and 525C". This value also corresponds to a position on each of every other scan that intersects with constant radial position line 525C of FIG. 5A, which is parallel to direction 244 of translation stage 242.) This retrieved value is compared to the signal from transducer 215 until it is determined that the values are equal, causing executables 372 to initiate clock pulse 532D. In the illustrated implementation, the radial position values in galvo position data table 378 are predetermined so that each of constant radial position lines 525 (e.g., 525A, 525B, through 525K of the example of FIG. 5A) are positioned at an equal distance perpendicular to direction 244. This feature facilitates the software translation of pixels from polar coordinates to Cartesian coordinates.

Thus, returning to the example of clock pulse 532D initiated at time t, it is illustratively assumed that filtered excitation signal 432 has a value at that time that is shown in FIG. 5D as filtered excitation voltage 580D. Voltage 580D therefore may be spatially correlated with radial position 525C' (and with the position at time t of translation stage 242). However, because voltage 580D has been filtered and thus phase delayed, it typically corresponds with values of gain-normalized excitation signal 422 that occurred earlier in time and therefore at a location on scan 520 to the left of radial position 525C'. To take into account this spatial translation, it is provided that adjusted emission signal 462 is phase delayed by the same amount. As noted, this result is accomplished by providing that the phase delay characteristics of filters 440 and 430 are matched. For example, the same electrical components may be used, particularly if gain generator 490 provides that adjusted emission signal 462 has approximately the same dynamic range as gain-normalized excitation signal 422. Thus, because the phase delays for both excitation and emission signals are the same, the value of filtered emission signal 442 sampled as the result of the initiation of clock pulse 532D, shown as illustrative voltage 550D in FIG. 5C, corresponds spatially with excitation voltage 580D. Alternatively stated, the matched filters provide that a fluorophore located at a position on probe feature 500 represented by position 525C', which was excited by voltage 580D, emitted a signal represented by voltage 550D, wherein both voltages were sampled at a same time.

A further desirable characteristic to be considered in the design of filters 430 and 440 is to provide constant group delay of the filters' input signals irrespective of the frequency components of those inputs. That is, it generally is desirable that the phase delay introduced by filters 430 and 440 be a determinable constant based on the filters' design rather than the characteristics of the input signal. Alternatively stated, it generally is desirable for bi-directional scanning that the rise and fall response characteristics of each of the filters be symmetrical. In the illustrated implementation, these characteristics are accomplished by providing that both of filters 430 and 440 are linear-phase filters, such as Bessel filters. In particular, filters 430 and 440 are high-order Bessel filters, such as $6^{th}$ order or higher, and preferably $11^{th}$ order or higher, Bessel filters. The advantage of providing the feature of symmetrical, matched filters may be illustrated with respect to the example of FIGS. 6A–6E.

Figure 6A:
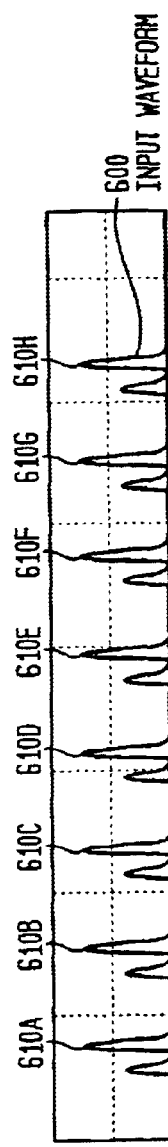
FIG. 6A is a graphical representation of a simulated input waveform including noise.

FIG. 6A shows a simplified input waveform 600 such as may be provided as input to filter 440, i.e., adjusted emission signal 462. Input waveform 600 has simulated high-frequency noise components that are included within repeating dual pulses 610A through 610G (generally and collectively referred to hereafter for convenience as noise pulses 610). It will be understood, however, that noise components of signal 462 (and of signal 422) typically are not regular and are more complex in frequency and amplitude.

Figure 6B:
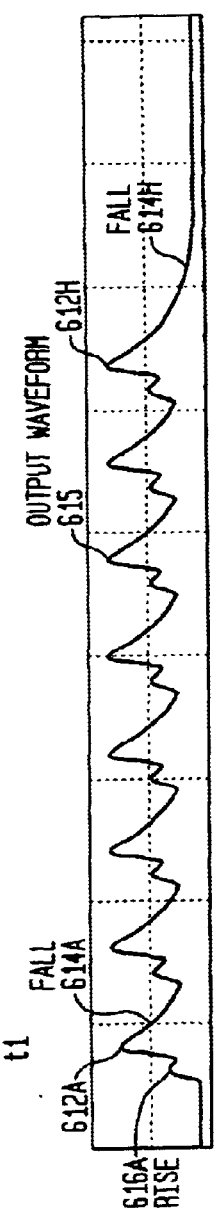
FIGS. 6B and 6C are graphical representations of output waveforms from alternative embodiments of asymmetrical filters responsive to the input waveform of FIG. 6A.

Output waveform 615 of FIG. 6B is a graphical representation of the output of filter 440 in response to input waveform 600, assuming that filter 440 is not a linear-phase filter. For example, filter 440 may be a Butterworth filter in this example. A peak 612A is observable on waveform 442A having a rising edge 616A that is steeper and of a different shape than its falling edge 614A; i.e., the rising and falling edges are not symmetrical. As is evident, the same asymmetry occurs in response to each of input pulses 610, as indicated by output pulses 612A through 612H.

Figure 6C:
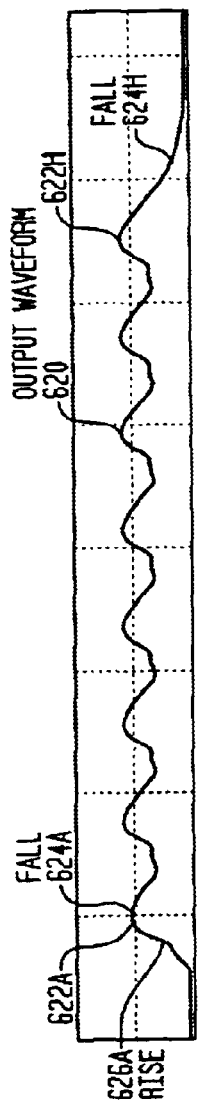

It is now illustratively assumed that output waveform 615 is the result of scan 520 in the left-to-right direction, and that a successive scan 522 in the opposite direction is made over a probe feature that has a constant concentration of fluorophores between and including the two scans. Equivalently, it may be assumed that the stepping motor does not advance translation stage 242 between the scans. To obtain the same result irrespective of the direction of the scan, output waveform 615 should have the same shape irrespective of which direction the scan was taken (although the waveforms will be displaced in time by a factor of twice the phase delay of the filter). However, as can be seen from FIG. 6B, this desired symmetry will not occur since the rising and falling edges of pulses 612 are asymmetrical. Improved smoothing and perhaps greater symmetry can be accomplished by higher-order filters that do not have the characteristic of constant group delay, as shown by FIG. 6C. Output waveform 620 of FIG. 6C is the response of such a filter to input waveform 600. Pulses 622 of FIG. 6C are smoother and somewhat more symmetrical than pulses 612 of FIG. 6B, but the problem of directional-dependent inconsistency remains.

Figure 6D:
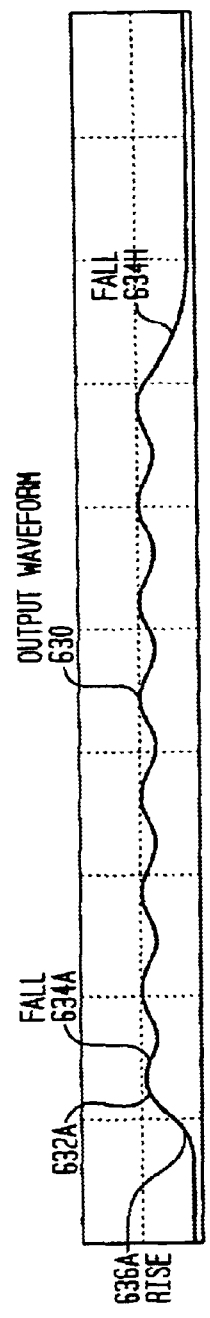
FIGS. 6D and 6E are graphical representations of output waveforms from alternative embodiments of symmetrical filters responsive to the input waveform of FIG. 6A.
Figure 6E:
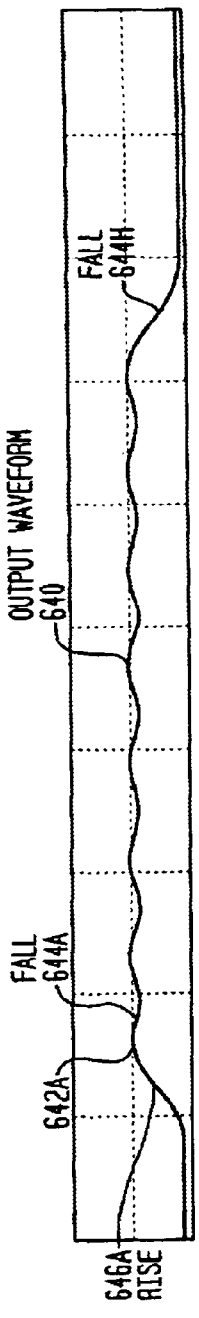

In contrast, output waveform 630 of FIGS. 6D is the simulated response of filter 440 implemented as a Bessel filter, and it may be observed that the resulting pulses are substantially symmetrical. For example, rising edge 636A is substantially the mirror image of falling edge 634H. The degree of symmetry generally may be improved by implementing filter 440 (and providing matched filter 430) as higher-order Bessel filters, as shown by output waveform 640 of FIG. 6E.

Figure 7A:
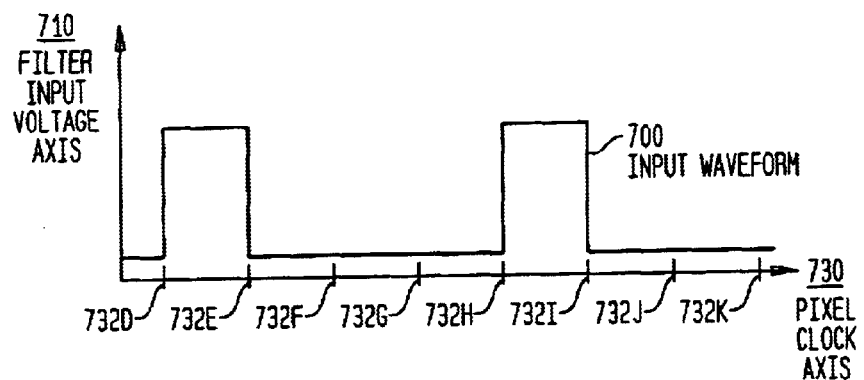
FIG. 7A is a graphical representation of an input waveform plotted as a function of pixel clock pulses.
Figure 7B:
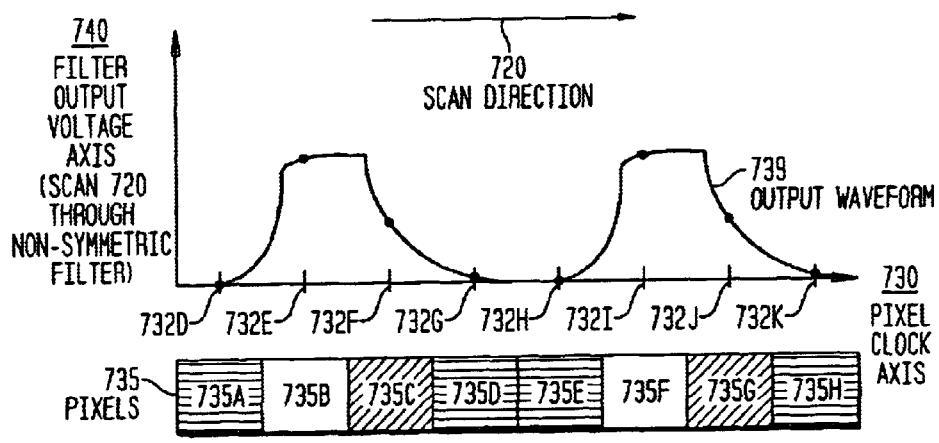
FIG. 7B is a graphical representation of an output waveform from one embodiment of an asymmetrical filter responsive to the input waveform of FIG. 7A as a function of pixel clock pulses in a sequence determined by scanning in a first direction.
Figure 7C:
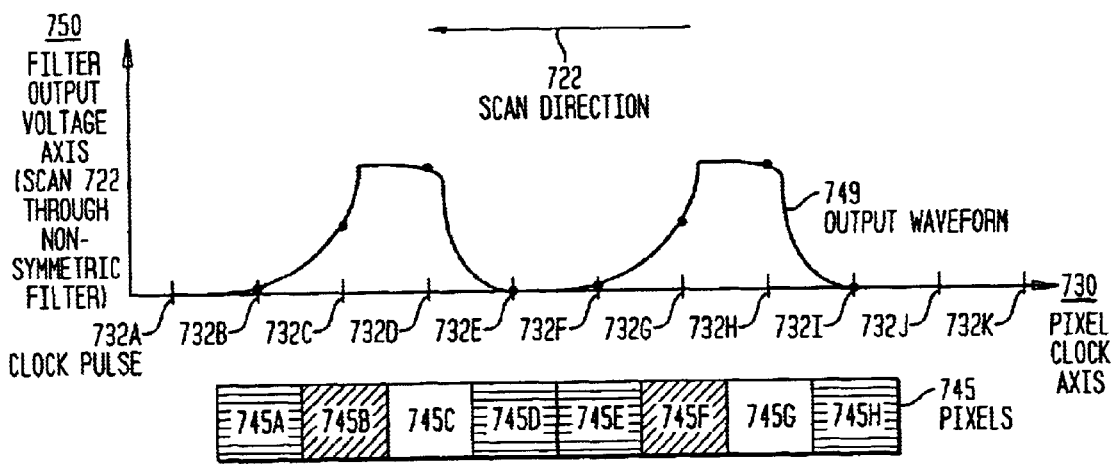
FIG. 7C is a graphical representation of an output waveform from the asymmetrical filter of FIG. 7B responsive to the input waveform of FIG. 7A as a function of pixel clock pulses in a sequence determined by scanning in a second direction opposite to the first direction.
Figure 8A:
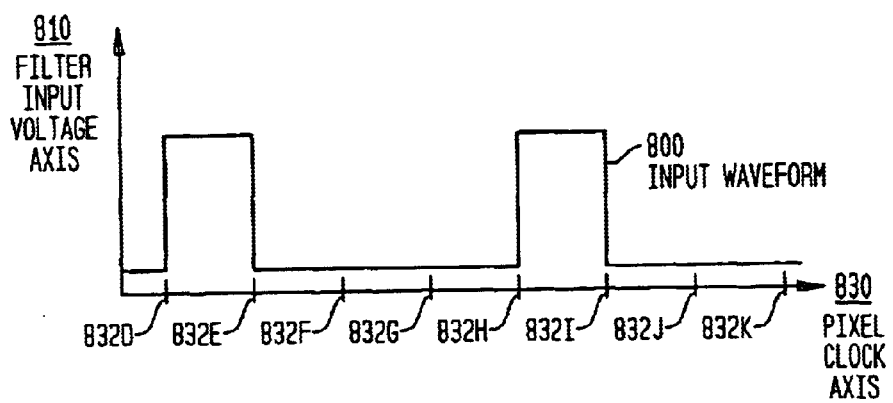
FIG. 8A is a graphical representation of an input waveform plotted as a function of pixel clock pulses.

The advantages of using symmetrical filters for bi-directional scanning may further be appreciated with reference to FIGS. 7A–7C and 8A–8C. FIG. 7A is a graphical representation of an input waveform 700 that is illustratively assumed to be provided to asymmetrical emission signal filter 440. Waveform 800 of FIG. 8A is the same as waveform 700, except that it is illustratively assumed to be provided to filter 440 implemented as a symmetrical filter, such as Bessel filters. Both waveforms 700 and 800 are idealized for clarity of illustration in that no noise is present and the pulses are shown as simple step functions.

Figure 8B:
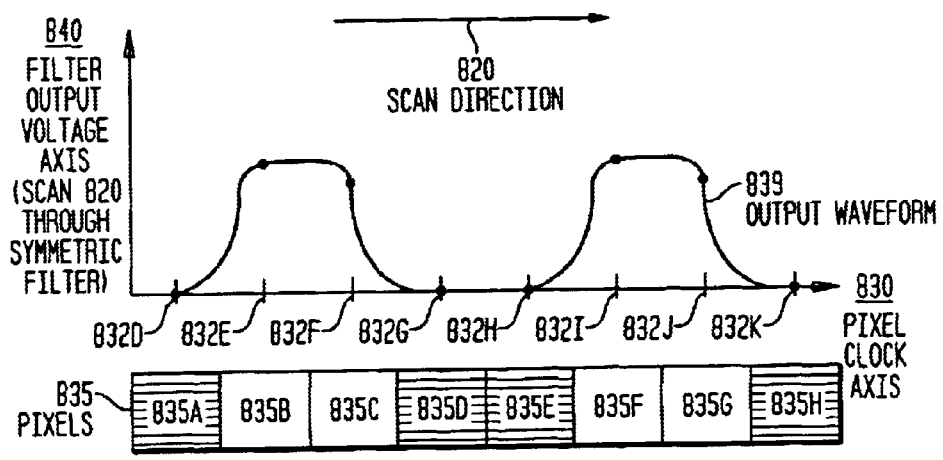
FIG. 8B is a graphical representation of an output waveform from one embodiment of a symmetrical filter responsive to the input waveform of FIG. 8A as a function of pixel clock pulses in a sequence determined by scanning in a first direction.
Figure 8C:
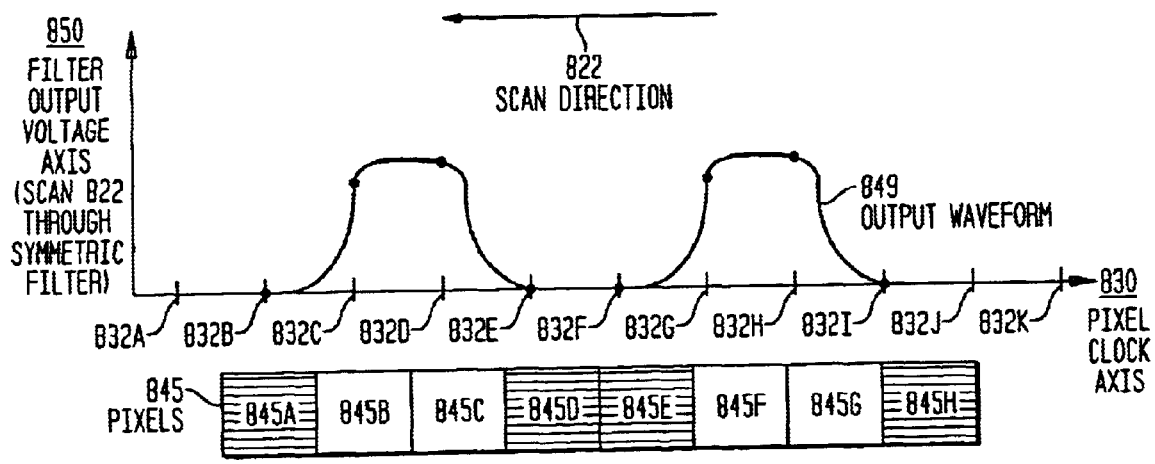
FIG. 8C is a graphical representation of an output waveform from the symmetrical filter of FIG. 8B responsive to the input waveform of FIG. 8A as a function of pixel clock pulses in a sequence determined by scanning in a second direction opposite to the first direction.

FIG. 7B shows output waveform 739 resulting from a scan 720 in a first direction, and FIG. 7C shows output waveform 749 resulting from a scan 522 in an opposite direction, both in the context of an implementation of filter 440 (and thus filter 430 to provide matching) as asymmetrical filters. Similarly, FIG. 8B shows output waveform 839 resulting from a scan 820 in a first direction, and FIG. 8C shows output waveform 849 resulting from a scan 522 in an opposite direction, both in the context of an implementation of filters 430 and 440 as symmetrical filters. The voltage waveforms of FIGS. 7A–7C and 8A–8C are shown as functions of consecutive clock pulses 732 and 832, respectively, on spatial pixel clock axes.

With reference to FIG. 7B, output waveform 739 results from scanning in left-to-right scan direction 720 in relation to spatial pixel clock axis 730. That is, input waveform 700 results from scanning at positions to the left of the radial position represented by pixel clock position 732D and proceeding toward the radial position represented by pixel clock position 732K. As seen from output waveform 739, the portion of the rising edge of that waveform between positions 732D and 732E is of a different shape than the portion of the falling edge between positions 732F and 732G. This difference is graphically represented by pixels 735 aligned below corresponding pixel clock positions. For example, if waveform 739 were sampled by a pixel clock pulse corresponding to position 732D, the sampled value would be relatively small. For convenience, a small value (e.g., relatively low intensity of filtered emission signal 442) is shown as a dark pixel, such as pixel 735A. If waveform 739 were sampled at position 732E, at the top of the rising edge, the sampled value would be relatively large, as represented by white pixel 735B indicating a high intensity emission signal. A sample taken at position 732F along the falling edge provides a middle value, as represented by pixel 735C in cross hatching. The area scanned in direction 720 between positions 732D and 732K would be represented by the following sequence of pixel intensities as indicated by pixels 735: dark-white-mid-dark-dark-white-mid-dark. Each level of intensity is indicative of a different degree of emission by fluorophores at locations corresponding to the pixel clock positions (although, as noted, a phase delay is anticipated). In FIG. 7C it is illustratively assumed that the same input waveform 700 is provided to the same filter, except that the scan is in direction 722, i.e., starting from position 732K and moving toward position 732D. Because of the asymmetry of the rising and falling edges after filtering, the samples taken in this reverse positional order result in a different sequence of pixel intensities, as indicated by pixels 745: dark-mid-white-dark-dark-mid-white-dark.

Two observations can thus be made by comparing these two sequences. One observation is that the two pulses of input waveform 700 are measured differently based on the direction of scanning: in the 720 direction the pulses are measured as white mid, whereas in the 722 direction the same pulses are measured as mid white. That is, in successive bid-directional scans, spatial transitions in input values provide inconsistent sampling results. The second observation is that the measured pulses are shifted spatially by twice the phase delay of the filter. This phase delay need not, and generally will not, be an integer number of pixel positions, but is a real number representing a spatial shift determined by the phase delay characteristics of the filter.

The results of these effects can be seen in FIG. 7D, which is a simplified graphical representation of pixels resulting from successive bi-directional scans of a probe feature in which adjusted emission signal 462 is represented by input waveform 700 for all scans in both directions. The pixels are aligned spatially along pixel clock axis 730, as in FIGS. 7B and 7C. In order to accommodate the phase delay introduced by emission filter 440, the spatial width of the scan in either direction (a distance D equal to the distance between ten clock pulses in this example) is greater than the spatial width of the probe feature being scanned (eight clock pulses); i.e., the feature can be said to have been over-scanned in both directions. Although the phase delay in this example is shown as equal to the distance between successive clock pulses, this is only an illustrative example. As noted, the delay in general is measured as a real number that may be expressed as fractions (any real number) of distances between clock pulses, i.e., fractional pixels.

FIG. 7E is a graphical representation of the pixels of FIG. 7D shifted so as to graphically compensate for the effects of phase delay. The pixels at the beginning and end of each scan have been eliminated from this representation so that the external edges of the feature representation can be more clearly seen. This shifted representation may, for example, be presented to users in a graphical user interface, or the data associating the pixels in this manner may be stored in computer 350 for further image and/or signal processing. These tasks may be accomplished in accordance with any of a variety of conventional techniques well known to those of ordinary skill in the art whether implemented in hardware, software, or a combination thereof. As indicated by FIG. 7E, transient pixel intensities appear indistinct. In particular, the left hand edge of the feature as represented by input waveform 700, as detected at the output of asymmetric filter 440 of this example, has a zipper-like pattern of alternating high and mid-intensities shown by vertically alternating pixels 735B and 745B. The right hand edge has the same distorted quality, as shown by vertically alternating pixels 735G and 745G. The same distortion is present at transient points within the feature, as indicated by vertically alternating pixels 735C and 745C, and by vertically alternating pixels 735F and 745F.

FIGS. 8D and 8E present the same information as described above with regard to FIG. 7D and 7E, respectively, except that FIGS. 8D and 8E are based on the assumption of FIG. 8B and 8C that filter 440 is a symmetrical filter. As is indicated by FIGS. 8D and 8E, a phase delay is also introduced by the symmetric filter. However, transients in the intensity of filtered emission signal 442 are not distorted. Rather, as indicated by the vertical alignment of consistently high-intensity pixels, the zipper effect is avoided and the transient points are clear.

Returning now to FIG. 4, two additional components of noise compensation module 310A remain to be described. Normalization factor generator 450 compares filtered excitation signal 432 to excitation reference 476. The purpose is to provide a normalization factor 452 that provides a measure of a deviation of filtered excitation signal 432 from a nominal value. This deviation typically is due to noise in excitation beam 135 generated by excitation source 120 (e.g., the laser operational at the period of interest) that thus appears in excitation signal 194 and gain-normalized excitation signal 422 and, in filtered form, in filtered excitation signal 432. The deviation may also be due, in some implementations, to long-term drift in excitation beam 135. For example, lasers may degrade over periods of weeks, months, or years so that the magnitude of their steady state output declines. This long-term drift, which may be positive or negative, may be compensated for by adjusting the gain of the appropriate one of gain generators 410B. Alternatively, the excitation reference component of calibration data 376 may be adjusted accordingly. In either case, if the long-term drift reaches a threshold level, a user may be advised that excitation source 120 has degraded and should be repaired or replaced. The threshold level may, for example, be a predetermined percentage of a nominal laser output value supplied by the laser manufacturer and stored as a component of calibration data 376. The notification to the user may be accomplished for example by an appropriate graphical user interface of computer 350, all in accordance with conventional techniques well known to those of ordinary skill in the relevant art.

With respect to the objective of compensating for laser noise, excitation reference 476 typically, but not necessarily, represents a nominal expected value of filtered excitation signal 432 over a time period substantially greater than that of the lowest expected noise frequency, but shorter than the time over which significant laser drift typically occurs. This period is selected such that an average or other statistical measure of signal 432 may reliably be determined. For example, monitored filtered excitation signal 434, equal to or representative of filtered excitation signal 432, may be provided to computer 350 for digital sampling over a period of one or more scans. In accordance with known techniques, the sampled signal may be statistically processed to provide, for example, an average or nominal value of signal 432 for that scan that may be used as excitation reference 476 for the next scan. Alternatively, each scan may be done twice: once to determine an average value and once to determine actual values including noise. Thus, the value of excitation reference 476 may be updated as frequently as every scan or less. Alternatively, reference 476 may be predetermined based on an initial calibration of excitation source 120, or based on manufacturer's specifications, and stored as a component of calibration data 376. In yet another alternative implementation, low-pass filter 431 may be used to remove all expected noise components from filtered excitation signal 432, and this low-frequency signal, shown as 476', may be used as an excitation reference. This implementation is represented in dashed lines in FIG. 4 to indicate its optional application.

As will now be appreciated by those of ordinary skill in the art, many other techniques are possible in hardware, software, or both, for providing an excitation reference that represents filtered excitation signal 432 with noise components substantially removed. In many cases, moreover, it is desirable to provide that, at a standard value of gain generator 490, each implementation of each excitation source 120 of each scanner 300 provides a standard value of filtered emission signal 442 when exciting a standard fluorophore sample. In some implementations, therefore, a known concentration of fluorophores is prepared as a calibration slide to be scanned by each of a series of manufactured scanners 300. Gain generator 490 is set at a nominal, standard, value, preferably one determined with respect to the dynamic range of the fluorophore. A photomultiplier tube or other detector is set to measure filtered emission signal 442. In some implementations, adjusted emission signal 462 may be measured instead. The power of excitation beam 135 is also measured by, for example, measuring filtered excitation signal 432 (with the corresponding gain generator 410 set to a standard value) in accordance with any of a variety of conventional measuring techniques. For each of excitation sources 120, e.g., for each of lasers 120A and 120B of the illustrated implementation, the excitation source is adjusted to increase or decrease excitation beam 135 until the measured value of filtered emission signal 442 (or of signal 462) is a standard value. The value of filtered excitation signal 432 at this calibration setting is stored in calibration data 376 and thenceforth serves as excitation reference 476 for that excitation source 120 for that scanner 130, or as a basis for determining an appropriate excitation reference. In alternative implementations, instead of adjusting the excitation source to increase or decrease beam 135, the adjustment may be made to gain generator 490, and/or to the gain of emission detector 115. In either case, excitation reference 476 is a constant value, and is not determined by, for example, averaging scans or low-pass filtering as described above. Rather, reference 476 is a calibrated value unique to the instrument and, generally, constant for the life of the instrument or a period of time over which consistent experimental results are desired. A significant advantage of the calibration approach leading to a constant excitation reference 476 for each scanner 130 instrument is that, even if excitation source 120 degrades over time, a user will be able to replicate experiments and obtain the same measurements over time.

In one implementation, normalization factor generator 450 may be an analog multiplier/divider device, such as is available from a variety of commercial suppliers including Analog Devices, Inc. of Norwood, Mass., or one of numerous other analog and/or digital devices that perform multiplication, division, and/or comparative functions. In the illustrated implementation, generator 450 multiplies or divides filtered excitation signal 432 and excitation reference 476 (or 476') to provide a ratio between the two. For example, if reference 476 has a value of 1.00 and the value of signal 432 is 1.25, then the value of normalization factor 452 at that time (hereafter, for convenience, the instantaneous value) is 1.00/1.25=0.80. That is, in this illustrative implementation, the comparison between a steady state measure of signal 432 and the instantaneous value of signal 432 is provided by dividing an average value of signal 430 by the instantaneous value of signal 430. Any of various other statistical comparisons may be used in alternative implementations, as will now be appreciated by those of ordinary skill in the relevant art.

Comparison processor 460 applies normalization factor 452 to filtered emission signal 442. Comparison processor 460 may also any of numerous analog multiplier/divider device or other devices such as noted above with respect to generator 450. In the illustrated implementation, processor 460 multiplies the instantaneous value of filtered emission signal 442 by normalization factor 452 to provide normalized emission signal 312. Thus, in the illustrated implementation, generator 450 and processor 460 together implement a function that may be represented as: signal 312(t)=signal 442(t)*(average signal 432/signal 432(t)) where (t) indicates instantaneous values over time.

Signal 312 may in some implementations be provided to computer 350 for sampling as enabled by pixel clock pulses generated by computer 350, as described above. In other implementations, the generation of pixel clock pulses and their application to signal 312 may be done by an appropriate device located in scanner 300. For example, as shown in FIG. 3, pixel clock 305 may be implemented in scanner 300 by a complex programmable logic device (CPLD) such as is commercially available from Altera Corporation of San Jose, Calif., and other suppliers.

Figure 9:
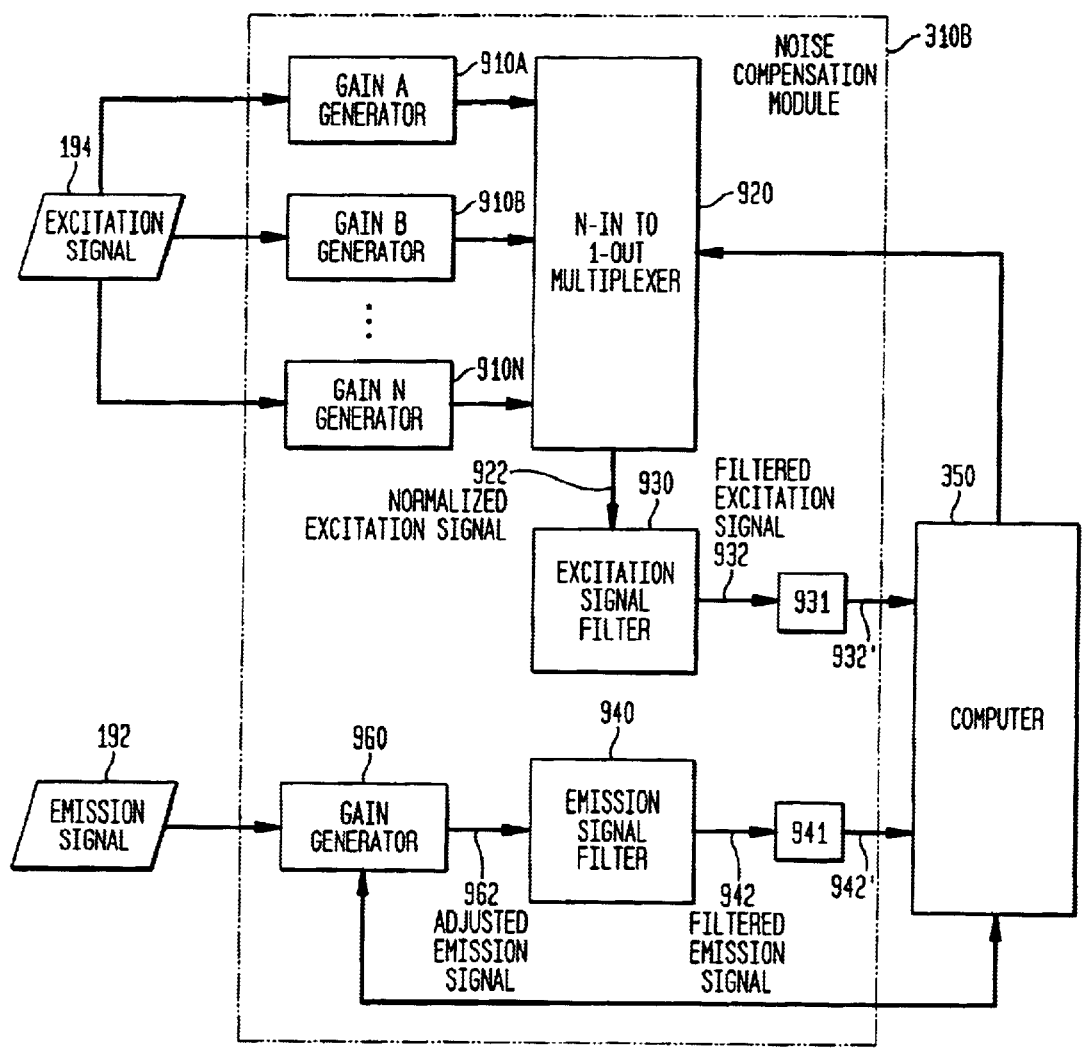
FIG. 9 is a functional block diagram of one embodiment of a noise compensation module for providing, together with a digital signal processing board and software on an associated computer, emission data normalized to compensate for noise in the excitation source.

FIG. 9 is a functional block diagram showing an alternative implementation in hardware and software of the functions just described with respect to the primarily hardware implementation of FIG. 4. In particular, the functions of elements 910, 920, 930, 940, and 960 of FIG. 9 are similar to those described above with respect to elements 410, 420, 430, 440, and 460 of FIG. 4, respectively. However, in the implementation of FIG. 9, the functions described above with respect to normalization factor generator 450 and comparison processor 460 are performed by computer 350. The result in the implementation of FIG. 9 is normalized emission signal data 374 that provide information similar to that contained in normalized emission signal 312 as shown in FIG. 4.

It will be understood that the embodiment of computer 350 shown in FIGS. 3, 4 and 9 is exemplary only, and that many alternative implementations are possible. For example, the functions of computer 350 may be performed by one or more components of scanner 300 rather than being performed by an external computer. instance, scanner 300 may include a microprocessor with associated firmware for performing some or all of the functions ascribed herein to computer 350.

In the illustrated embodiment, computer 350 may be located locally to scanner 300, or it may be coupled to scanner 300 over a local-area, wide-area, or other network, including an intranet and/or the Internet. Computer 350 may be a personal computer, a workstation, a server, or any other type of computing platform now available or that may be developed in the future. As shown in FIG. 4, computer 350 includes a process controller 462 for performing control and analysis functions with respect to scanner 300 as described below. Typically, computer 350 also includes known components such as CPU 355, operating system 360, system memory 370, memory storage devices 380, and input-output controllers 375, all of which typically communicate in accordance with known techniques such as via system bus 390. In the illustrated implementation, computer 350 also includes digital signal processor board 380, which may be any of a variety of PC-based DSP controller boards, such as the M44 DSP Board made by Innovative Integration of Simi Valley, Calif. A variety of other components may be included in computer 350, as is well known by those of ordinary skill in the relevant art.

In reference to FIG. 9, filtered excitation signal 932, corresponding to filtered excitation signal 432 described above, is provided to line driver 931 that, in accordance with known techniques, provides signal 932' to DSP board 380 of computer 350. Similarly, filtered emission signal 942, corresponding to filtered emission signal 442 described above, is provided to line driver 941 that provides signal 942' to DSP board 380. In accordance with known analog-to-digital sampling techniques, board 380 samples signals 932' and 942' based on pixel clock sampling pulses. These pulses may be provided by pixel clock CLPD 305, or they may be generated by aspects of executables 372 by comparing radial position information from galvo position transducer 215 with data in galvo position data table 378. In the former implementations, CLPD 305 performs the functions of computer 350, and may also store data such as that in table 378. Optionally, prior to sampling, board 380 may include anti-aliasing filters (such as filters 1030 and 1040 of FIG. 10) designed in accordance with the Nyquist criterion as noted above to further ensure that aliasing errors do not occur when signals 932' and 942' are sampled.

In this alternative implementation software-implemented functional elements of executables 372 perform the functions described in reference to FIG. 4 with respect to the operations of normalization factor generator 450 and comparison processor 460. That is, executables 372, in cooperation with other elements of computer 350 such as CPU 355 and operating system 380, generates a compensation factor that is based on a comparison between a reference excitation value and, in some implementations, each sampled excitation value. Executables 372 then applies this factor to each corresponding sampled emission signal to provide normalized emission signal data corresponding to each sample of the emission signal. Thus, the functional elements of executables 372 comprise sets of software instructions that cause the described functions to be performed. These software instructions may be programmed in any programming language, such as C++or another high-level programming language. Executables 372 may therefore be referred to as a set of scanner control and analyzing instructions, and its functional elements may similarly be described, for example, as sets of normalization factor generating instructions (as represented by generator 1050) and comparison processing instructions (as represented by processor 1060).

Figure 10:
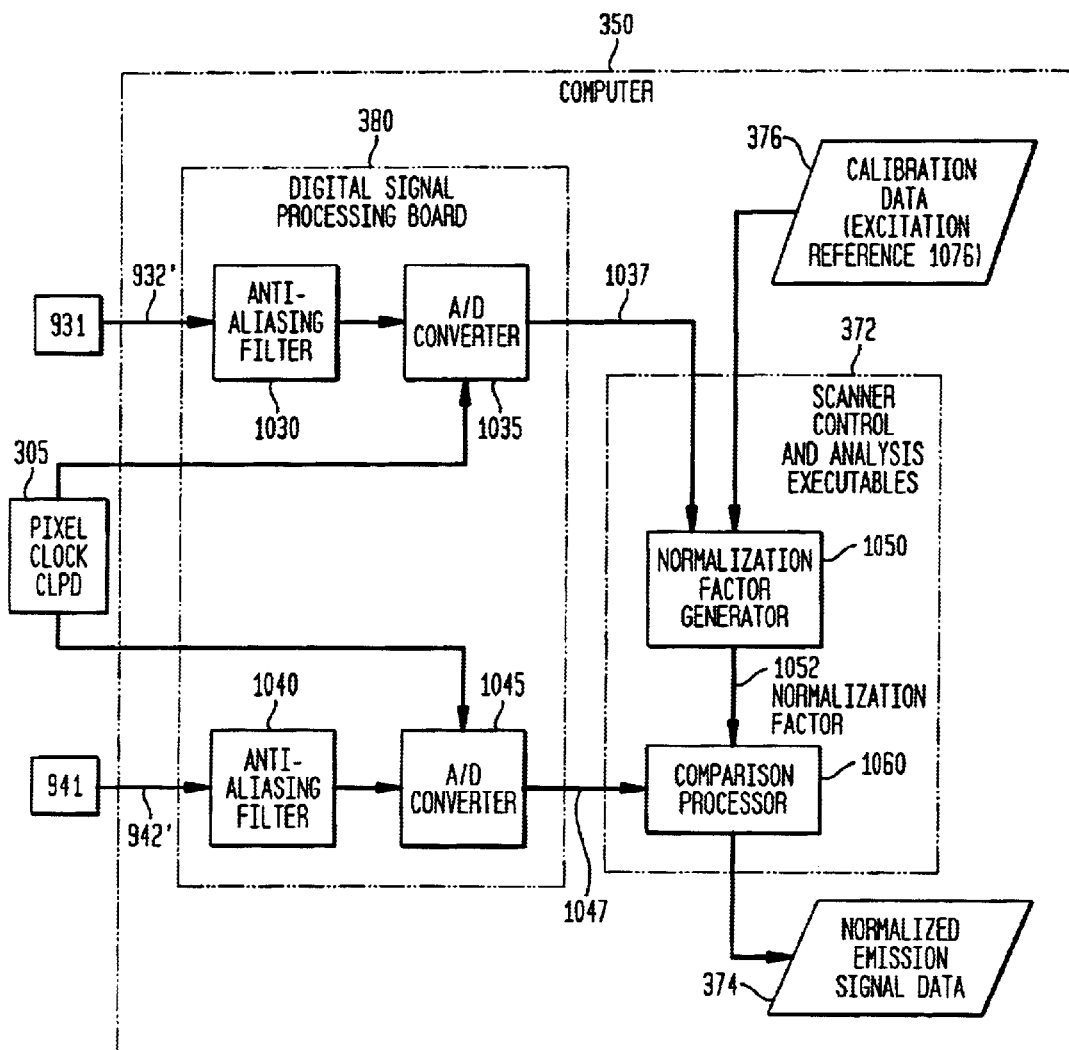
FIG. 10 is a functional block diagram of one embodiment of aspects of a computer of the scanner-computer system of FIG. 3 suitable for generating normalized emission signal data.

These operations are shown in greater detail in FIG. 10, which is a functional block diagram of aspects of computer 350 that generate normalization factors for each sampled excitation signal and applies those factors to filtered emission signals to obtain normalized emission signal data. In accordance with any of a variety of known techniques, analog to digital converter 1035 digitizes samples of signals 932' to generate excitation samples 1037, which are provided by to normalization factor generator 1050 of executables 372. Similarly, analog to digital converter 1045 digitizes samples of signals 942' to generate emission samples 1047, which are provided by to comparison processor 1060 of executables 372. For ease of reference, a pair of samples 1037 and 1047 sampled according to the same sampling pulse will be referred to as a particular instance of those samples.

Excitation reference 1076 of calibration data 376 also is provided to generator 1050. Reference 1076 is a reference excitation value derived in accordance with any the techniques described above with respect to excitation reference 476.

Generator 1050 performs functions similar to those described above with respect to generator 450. For example, in some implementations, generator 1050 determines an instance of compensation factor 1052 by dividing reference 1076 by the value of excitation sample 1037 for that instance. This instance of factor 1052 is multiplied by the corresponding instance of emission sample 1047 to obtain the corresponding instance of normalized emission signal data 374. Thus, in the illustrated and non-limiting implementation, each instance (I) of data 374 is derived in accordance with the algorithm: data 374(I)=sample 1047(I)* (reference 1076/ sample 1037(I)) Typically, generator 1060 and processor 1070 are implemented as software instructions in any appropriate programming language, such as C++, and compiled for inclusion in executables 372 that are executed on computer 350 of the illustrated implementation. In particular, system memory 370 of computer 350 may be any of a variety of known or future memory storage devices. Examples include any commonly available random access memory (RAM), magnetic medium such as a resident hard disk or tape, an optical medium such as a read and write compact disc, or other memory storage device. Memory storage devices 380 may be any of a variety of known or future devices, including a compact disk drive, a tape drive, a removable or internal hard disk drive, or a diskette drive. Such types of memory storage devices 380 typically read from, and/or write to, a program storage medium (not shown) such as, respectively, a compact disk, magnetic tape, removable or internal hard disk, or floppy diskette. Any of these program storage media, or others now in use or that may later be developed, may be considered a computer program product. As will be appreciated, these program storage media typically store a computer software program and/or data. Computer software programs, also called computer control logic, typically are stored in system memory and/or the program storage medium used in conjunction with memory storage devices 380.

In some implementations, a computer program product is described comprising a computer usable medium having control logic (computer software program, including program code) stored therein. The control logic, when executed by processor 355, causes processor 355 to perform the functions of scanner control and analysis executables 372, including generator 1050 and processor 1060. In other embodiments, these and other functions of executables 372 may be implemented primarily in hardware using, for example, a hardware state machine. Implementation of the hardware state machine so as to perform the functions of executables 372 described herein will be apparent to those skilled in the relevant art.

Having described various embodiments and implementations, it should be apparent to those skilled in the relevant art that the foregoing is illustrative only and not limiting, having been presented by way of example only. Many other schemes for distributing functions among the various functional elements of the illustrated embodiment are possible. The functions of any element may be carried out in various ways in alternative embodiments.

Also, the functions of several elements may, in alternative embodiments, be carried out by fewer, or a single, element. For example, excitation signal filter 430 emission signal filter 440 of the implementation shown in FIG. 4 may, in other implementations, be replaced by a single anti-aliasing filter that operates on the output of comparison processor 460 to provide normalized emission signal 312. As another example, the functions of gain generators 410 could alternatively be performed by multiplexer 420, or by computer 350.

Similarly, in some embodiments, any functional element may perform fewer, or different, operations than those described with respect to the illustrated embodiment. Also, functional elements shown as distinct for purposes of illustration may be incorporated within other functional elements in a particular implementation. Furthermore, the sequencing of functions, or portions of functions, generally may be altered. For instance, the functions of gain generator 490 may be performed after those of emission signal filter 440.

Certain functional elements, files, data structures, and so on, are described in the illustrated embodiments as located in system memory 370 of computer 350. In other embodiments, however, any or all of these may be located on, or distributed across, computer systems or other platforms that are co-located and/or remote from each other. In addition, it will be understood by those skilled in the relevant art that control and data flows between and among functional elements and various data structures may vary in many ways from the control and data flows described above. More particularly, intermediary functional elements may direct control or data flows, and the functions of various elements may be combined, divided, or otherwise rearranged to allow parallel processing or for other reasons. Also, intermediate data structures or files may be used and various described data structures or files may be combined or otherwise arranged. Numerous other embodiments, and modifications thereof, are contemplated as falling within the scope of the present invention as defined by appended claims and equivalents thereto.

What is claimed is:

1. A method for analyzing molecules, comprising the steps of:
   (1) directing an excitation beam to a plurality of probe locations;
   (2) receiving an emission signal;
   (3) linear-phase filtering the emission signal to provide a filtered emission signal having substantially symmetrical rise and fall edges; and
   (4) analyzing molecules at one or more probe locations based, at least in part, on one or more values of the filtered emission signal.

2. An apparatus comprising:
   an excitation beam provider constructed and arranged to direct an excitation beam to a plurality of locations of a probe array;
   an emission signal detector constructed and arranged to detect an emission signal from at least one location; and
   an emission filter comprising a linear-phase filter constructed and arranged to filter the emission signal to provide a filtered emission signal having substantially symmetrical rise and fall edges.

3. The apparatus of claim 2, further comprising:
   an excitation signal detector constructed and arranged to detect an excitation signal; and
   an excitation filter constructed and arranged to filter the excitation signal to provide a filtered excitation signal.

4. The apparatus of claim 3, wherein:
   the emission filter and the excitation filter are matched with each other.

5. The apparatus of claim 3, wherein:
   the emission filter has a first delay function and the excitation filter has a second delay function; and the apparatus further comprises a delay compensator constructed and arranged to compensate for a difference between the first and second delay functions, if any.

6. The apparatus of claim 3, wherein:
   the excitation filter comprises a linear-phase filter constructed and arranged to filter the excitation signal to provide a filtered excitation signal having substantially symmetrical rise and fall edges.

7. The apparatus of claim 6, wherein:
   the emission filter and the excitation filter both comprise a high-order Bessel filter.

8. The apparatus of claim 7, wherein:
   the Bessel filter is a sixth or higher order Bessel filter.

9. The apparatus of claim 7, wherein:
   the Bessel filter is an eleventh or higher order Bessel filter.

10. The apparatus of claim 2, wherein:
    the emission filter further is constructed and arranged to normalize the emission signal to avoid aliasing errors.

11. The apparatus of claim 2, wherein:
    the emission filter comprises a low-pass, anti-aliasing filter.

12. The apparatus of claim 11, wherein:
    one or more characteristics of the emission filter are determined, at least in part, based on a scan rate or a resolution.

13. The apparatus of claim 11, wherein:
    a low-pass characteristic of the linear-phase emission filter is determined, at least in part, based on applying the Nyquist criterion to a sampling rate.

14. The apparatus of claim 2, further comprising:
    a clock signal generator constructed and arranged to generate a clock signal to digitize the filtered emission signal, thereby providing a plurality of digitized emission values.

15. The apparatus of claim 14, further comprising:
    an excitation signal detector constructed and arranged to detect an excitation signal indicative of the excitation beam; and
    an excitation filter constructed and arranged to filter the excitation signal to provide a filtered excitation signal;
    wherein the clock signal digitizes the filtered excitation signal, thereby providing a plurality of digitized excitation values.

16. The apparatus of claim 15, wherein:
    the emission filter and the excitation filter are matched so that the plurality of digitized emission values are spatially correlated with the plurality of digitized excitation values.

17. The apparatus of claim 2, wherein:
    the excitation beam provider further is constructed and arranged to direct the excitation beam to the plurality of locations of the probe array so that dx/dt is substantially constant.

18. The apparatus of claim 2, wherein:
    the probe array comprises a synthesized probe array.

19. The apparatus of claim 2, wherein:
    the probe array comprises a spotted probe array.

20. A method comprising the steps of:
    detecting an emission signal from a probe array; and
    filtering the emission signal to provide a filtered emission signal having substantially symmetrical rise and fall edges.

21. The method of claim 20, further comprising the step of:
  directing an excitation beam to a plurality of locations of the probe array, thereby giving rise to the emission signal.

22. The method of claim 21, further comprising the step of:
  detecting an excitation signal indicative of the excitation beam; and
  filtering the excitation signal to provide a filtered excitation signal.

23. The method of claim 21, wherein:
  filtering the excitation signal includes linear-phase filtering to provide a filtered excitation signal having substantially symmetrical rise and fall edges.

24. The method of claim 20, further comprising the step of:
  digitizing the filtered emission signal, thereby providing a plurality of digitized emission values.

25. The method of claim 20, wherein:
  the probe array comprises a synthesized probe array.

26. The method of claim 20, wherein:
  the probe array comprises a spotted probe array.

27. A noise compensation module comprising:
  an excitation signal filter constructed and arranged to filter at least a first and a second excitation signal; and
  an emission signal filter constructed and arranged to filter at least a first and a second emission signal;
  wherein the excitation signal filter and the emission signal filter are linear-phase filters, the first excitation signal and corresponding first emission signal are derived from a scan in a first direction, and the second excitation signal and corresponding second emission signal are derived from a scan in a second direction that is opposite to the first direction.

28. The noise compensation module of claim 27, wherein:
  the excitation signal filter and the emission signal filter are matched with each other.

29. The noise compensation module of claim 27, wherein:
  the excitation signal filter and the emission signal filter both comprise a high-order Bessel filter.

30. A method comprising the steps of:
  filtering at least a first and a second excitation signal; and
  filtering at least a first and a second emission signal;
  wherein the filtering characteristics applied to the first and second excitation signals and to the first and second emission signals are linear-phase, the first excitation signal and corresponding first emission signal are derived from a scan in a first direction, and the second excitation signal and corresponding second emission signal are derived from a scan in a second direction that is opposite to the first direction.

31. An apparatus comprising:
  an emission signal detector constructed and arranged to detect an emission signal from at least one probe; and
  an emission filter constructed and arranged to filter the emission signal to provide a filtered emission signal having substantially symmetrical rise and fall edges.

32. A method comprising the steps of:
  detecting an emission signal from at least one probe; and
  filtering the emission signal to provide a filtered emission signal having substantially symmetrical rise and fall edges.

* * * * *